United States Patent
Qiu et al.

(10) Patent No.: US 7,232,616 B2
(45) Date of Patent: Jun. 19, 2007

(54) ORGANIC ELECTROLUMINESCENT MATERIALS AND DEVICES MADE FROM SUCH MATERIALS

(75) Inventors: Yong Qiu, Beijing (CN); Juan Qiao, Beijing (CN)

(73) Assignee: Tsinghua University, Beijing (CN)

( * ) Notice: Subject to any disclaimer, the term of this patent is extended or adjusted under 35 U.S.C. 154(b) by 0 days.

(21) Appl. No.: 10/352,493

(22) Filed: Jan. 28, 2003

(65) Prior Publication Data

US 2004/0001970 A1 Jan. 1, 2004

(30) Foreign Application Priority Data

Jun. 13, 2002 (CN) ............... 02 1 21289
Oct. 23, 2002 (CN) ............... 02 1 45923

(51) Int. Cl.
H01L 51/54 (2006.01)
C09K 11/06 (2006.01)

(52) U.S. Cl. ............ 428/690; 428/917; 252/301.16; 313/504; 546/5; 546/6; 546/7; 546/10; 544/225; 548/106; 548/108; 556/32; 556/33; 556/40; 556/178

(58) Field of Classification Search ........... 252/301.16; 313/504, 506, 503, 509; 428/917, 690; 556/33, 556/32, 40, 178; 546/2, 7, 10, 6, 5; 544/225; 548/101, 106, 108

See application file for complete search history.

(56) References Cited

U.S. PATENT DOCUMENTS 5,580,527 A * 12/1996 Bell et al. ............ 422/82.07

5,731,147 A * 3/1998 Bard et al. ............ 435/6
6,126,996 A * 10/2000 Kirlin et al. ............ 427/252

(Continued)

OTHER PUBLICATIONS

Albrecht et al., An ethylene-linked catechol/8-hydroxyquinoline derivtive and its dinuclear gallium (II) complex, The Royal Society of Chemistry and the Centre National de la Rechereche Scientificque 2000 (24), pp. 619-622.*

(Continued)

Primary Examiner—Marie Yamnitzky
Assistant Examiner—Camie S. Thompson
(74) Attorney, Agent, or Firm—RatnerPrestia

(57) ABSTRACT

A class of organic metal complexes with mixed ligands for organic light emitting diodes are designed and characterized as the formula:$(L^2L^3M)n$. In this formula: $L^2$ is a bidentate ligand which has at least one coordinate atom of oxygen; $L^3$ is a tridentate ligand with three chelate points; M is trivalent metal selected from the group consisting of Al, Ga, In, Tl, and Ir; and n is an integer of from 1 to 2. In Formula (3), X, Y independently represent CH or N and II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, pyridine, etc. These complexes can be used as emitting materials or electron transporting materials in organic EL devices

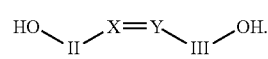

Formula (3)

25 Claims, 4 Drawing Sheets

U.S. PATENT DOCUMENTS

| | | | |
|---|---|---|---|
| 6,278,056 B1 * | 8/2001 | Sugihara et al. | 136/263 |
| 6,410,766 B2 * | 6/2002 | Qiu et al. | 556/33 |
| 6,565,994 B2 * | 5/2003 | Igarashi | 428/690 |
| 6,699,717 B1 * | 3/2004 | Rao et al. | 436/39 |

OTHER PUBLICATIONS

Ma et al., A dinuclear aluminum 8-hydroxyquinoline coplex with high electron mobility for organic light emitting diodes, Applied Physics Letters, 2003(82), pp. 1296-1298.*

Qiao et al., Pure red electroluminescence from a host material of binuclear gallium complex, Applied Physics Letters, vol. 81, No. 26.*

Yan Shao et al., "A Novel Asymmetric Complex for Organic Electroluminescence," *Advanced Materials for Optics and Electronics*, vol. 10, Issue 6, 2000, pp. 285-288.

* cited by examiner

ORGANIC ELECTROLUMINESCENT MATERIALS AND DEVICES MADE FROM SUCH MATERIALS

BACKGROUND OF THE INVENTION

1. Field of the Invention

This invention relates to novel luminescent materials, and more particularly, this invention relates to a novel class of luminescent materials of metal chelates with mixed ligands and organic electroluminescent (EL) devices made from such materials.

2. Description of the Related Art

During the last decade, an explosive growth of activity in the area of organic electroluminescence has occurred in both academia and industry, stimulated by the promise of light-emitting plastics for the fabrication of large, flexible, inexpensive and efficient screens to be used in different applications. A great deal of work has been carried out by physicists and materials scientists concerned with the preparation of different device structures and with the use of different techniques for device manufacture. The design of luminescent materials for use in LED devices is as critical to device performance as the process of constructing the device itself. Processability, purity, thermal and oxidative stability, color of emission, luminance efficiency, balance of charge carrier mobility, and others are among many important materials properties required for a system to be viable in commercial LED device applications. As a result, numerous organic compounds intended for OLEDs have been developed in the past decade.

Organometallic complex luminescent materials for use in organic electroluminescent (EL) devices have been reported. Commonly-assigned U.S. Pat. No. 4,720,432 issued Jan. 19, 1988, discloses the efficient organic EL devices using the organometallic complex, metal chelates of 8-quinolinolato ligands, as a luminescent medium. Tris(8-hydroxyquinoline) aluminum ($Alq_3$) is a stable metal chelate that can be sublimed to yield amorphous thin films and stands as one of the most successful organic materials used in OLEDs. And many derivatives of $Alq_3$ have been investigated as emitter materials, including substitution of the metal ion with other trivalent metals ($M^{+3}$=Ga, In, and Sc) and substitution of the 8-quinolinol ligand (substituent=F, Cl, CN, and alkyl groups). However, most of the previous work on metal-chelate EL complexes have focused on system with one kind of ligand such as $Alq_3$, and much less attention has been directed toward metal systems containing two different ligands. This type of EL material is expected to be amorphous due to the asymmetric structure of the molecular constituents.

In our group, we focused on metal(III) complexes based on tridentate schiff-base ligands, which have proven to be high efficient luminescent materials for OLEDs. Some preliminary communication of this work has been reported on (salicylidene-o-aminophenolato)(8-quinolinato) aluminum (Al(Saph)-q) and its derivatives for the first time by Y. Shao and Y. Qiu et al. in Adv. Mater. Opt. Electro. 2000, 10, 285, and U.S. Pat. No. 6,410,766 issued in Jun. 25, 2002. It has been proven that the introduction of the tridentate schiff-base ligand could greatly improve the thermal stability and film-forming capability of aluminum complexes for organic EL.

SUMMARY OF THE INVENTION

Accordingly, a first object of the present invention is to provide novel series of organic metal complexes based on many kinds of tridentate ligands and bidentate ligands. Along with changing the central ions and the ligands, a novel class of metal complexes, dimeric organic metal complexes have been designed and characterized. These complexes exhibited strongly luminescent properties and excellent film-forming capability, which are conducive to achieving high performance organic EL devices.

A second object of the present invention is to provide an electroluminescent device in which such novel complexes have been used. These materials can be used not only as emitting materials but also as electron-transporting materials to produce EL devices with a wide range of visible colors, especially as host material for the variable dopants in doped OLEDs. Moreover, some of these complexes show outstanding solution processability, the relative devices can be fabricated by spin coating or ink-jet besides commonly vacuum evaporation.

This invention disclosed here a novel class of organic metal complexes based on tridentate ligands. From the aspect of molecular structure, these complexes have asymmetric structures with mixed ligands, which are largely different with the typical $Alq_3$. Moreover, most of them are dimers of organic metal complexes, in one or other way, which represent a novel class of materials for organic EL. As a result, these materials exhibited some unique characteristics that will be conducive to high performance organic EL devices. The advantage of these materials lies in much higher luminescent efficiencies and better film-forming capability than the typical $Alq_3$. And organic light emitting diodes (OLEDs) based on these complexes display high performance such as low turn-on voltages and high efficiency.

In one aspect, this invention relates to a novel class of luminescent materials of metal chelates having variable tridentate ligands.

In another aspect, this invention relates to a novel class of luminescent materials of metal chelates having variable tridentate ligands and capable of emitting visible light luminescence.

In a further aspect, this invention relates to a novel class of luminescent materials of metal chelates having variable tridentate ligands and capable of using as components in organic EL devices.

The invention is particularly suitable for use in organic electroluminescent (EL) devices but is also suitable for use as an electron transporting carrier, which can also be used in EL devices and other electro-optical devices. Moreover, it can be used in photoconductive elements particularly suitable in electrophotographic copying applications.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
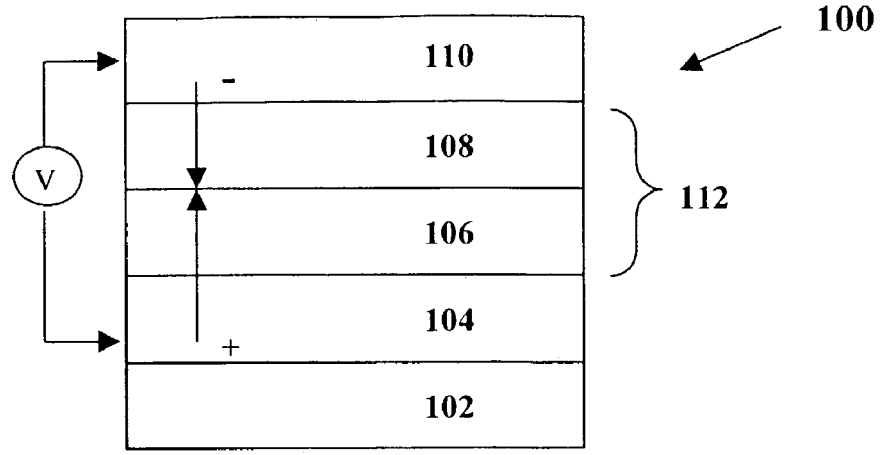
FIGS. 1, 2, 3 are schematic diagrams of the multi-layer structures of preferred EL devices in accordance with the present invention.

The present invention is particularly suitable for use in EL devices and so those applications will now be discussed. An exemplary EL device 100 according to the invention is schematically illustrated in FIG. 1. The support is layer 102, which is an electrically insulating and optically transparent material such as glass or plastic. Anode 104 is separated from cathode 110 by an organic EL medium 112, which, as shown, consists of two superimposed layers of organic thin films. Layer 106 located on the anode forms a hole-transport layer of the organic EL medium and layer 108 as emitting and electron transport layer. The anode and the cathode are connected to an external AC or DC power source. The power source can be pulsed, periodic, or continuous.

In operation, the EL device can be viewed as a diode which is forward biased when the anode is at a higher potential than the cathode. Under these conditions, holes (positive charge carriers) are injected from the anode into the hole-transport layer, and electrons are injected into the electron-transport layer. The injected holes and electrons each migrate toward the oppositely charged electrode, as shown by the arrows, respectively. This results in hole-electron recombination and a release of energy in part as light, thus producing electroluminescence.

Figure 2:
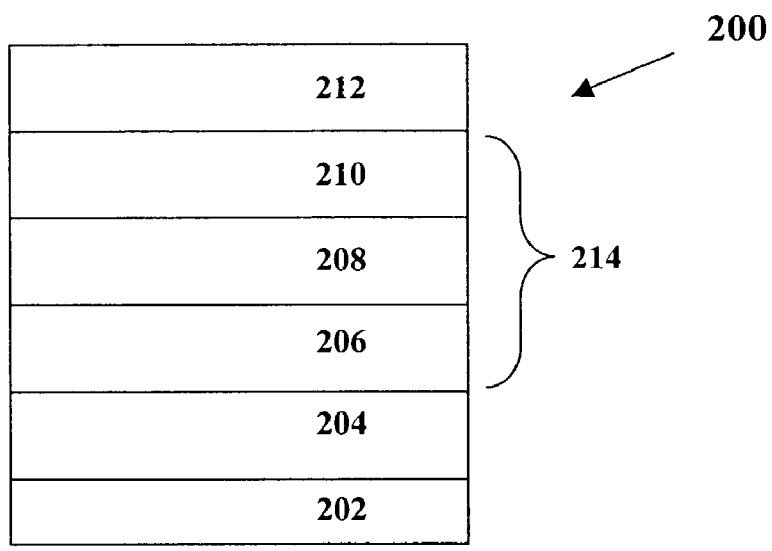

Organic EL device 200 shown in FIG. 2 is illustration of another preferred embodiment of the invention. The insulating and transparent support is layer 202. The anode 204 is separated from the cathode 212 by an EL medium 214, which, as shown, consists of three superimposed layers of organic thin films. Layer 210 adjacent to cathode 212 is the electron-transport layer. Layer 208 is the luminescent layer, between the hole-transport layer 206 and the electron-transport layer 210. This luminescent layer also serves as the recombination layer where the hole and electron recombines.

Figure 3:
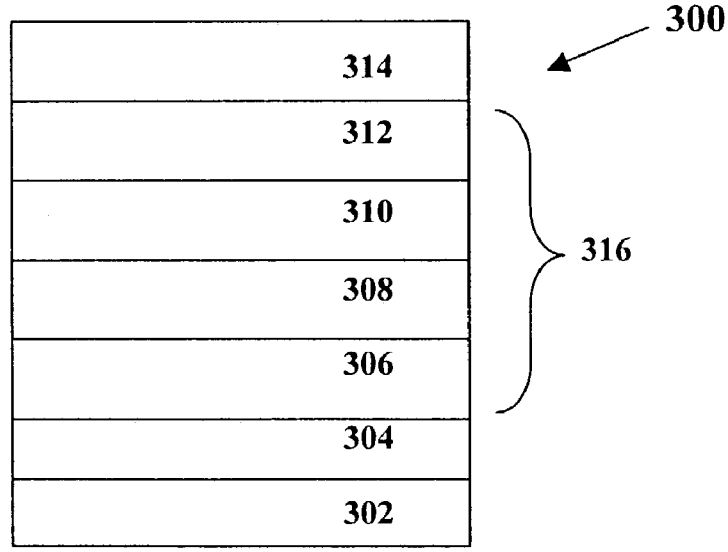
Figure 4A:
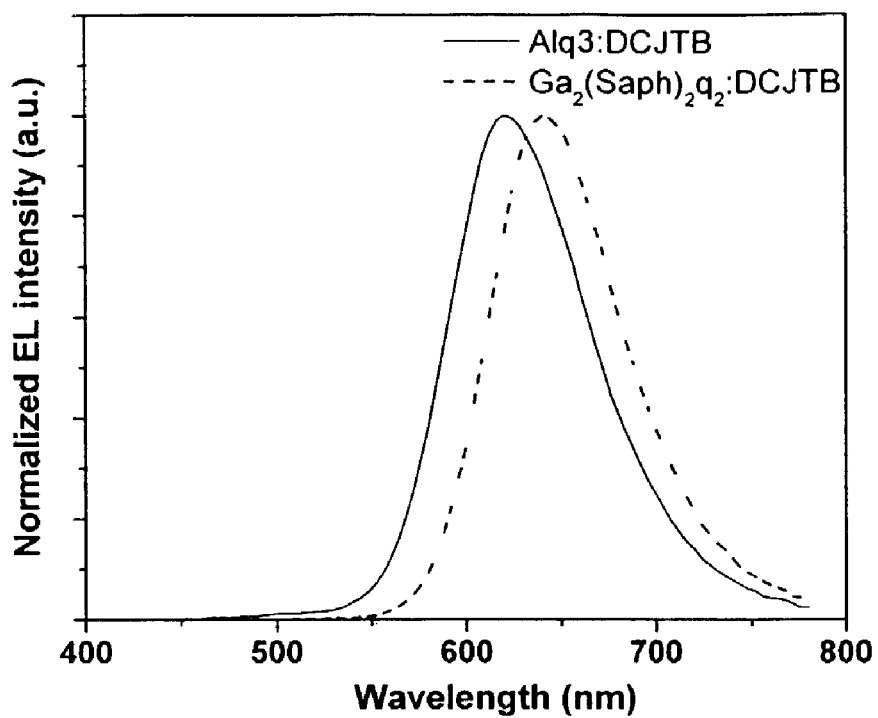
FIG. 4A and FIG. 4B are the EL spectra and the color position in the color coordinates system (CIE1931) for the device comprising $Ga_2(saph)_2q_2$, with the following layer structure: ITO/NPB (30 nm)/Ga$_2$(saph)$_2$q$_2$:DCJTB(2%; 40 nm)/Ga$_2$(saph)$_2$q$_2$(15 nm)/Mg:Ag(10:1).
Figure 4B:
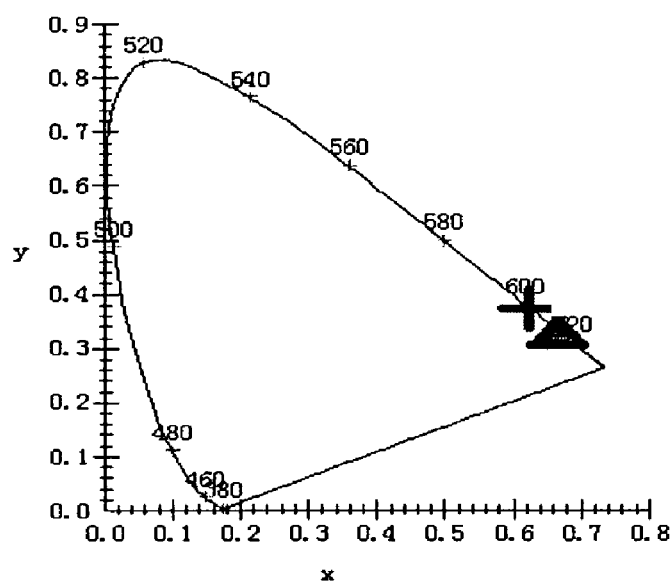
Figure 5:
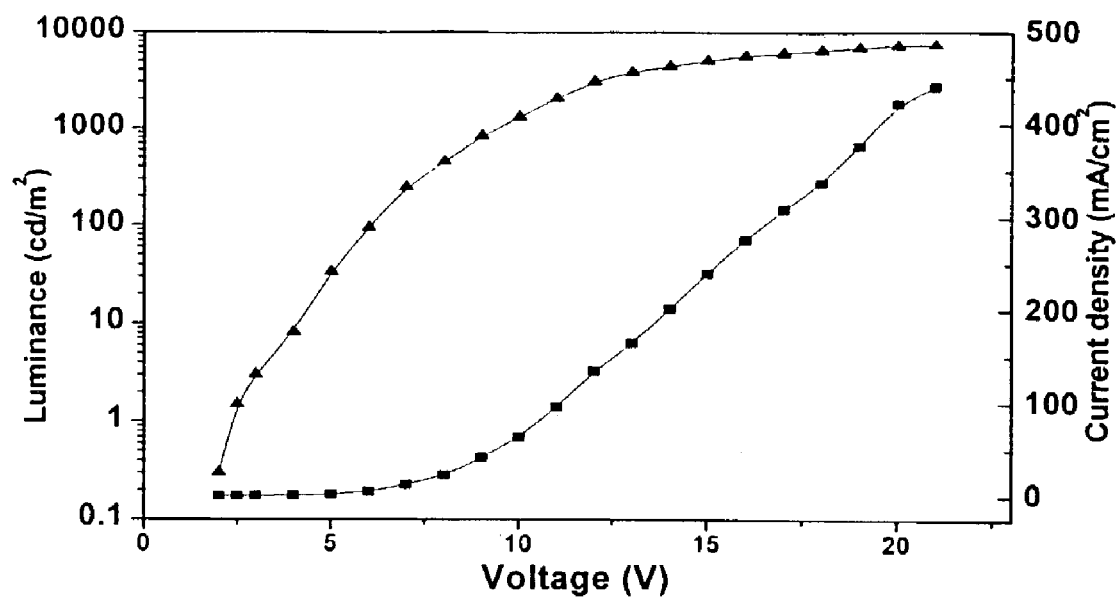
FIG. 5 is the Current-Luminance-Voltage curves of the device comprising Ga$_2$(saph)$_2$q$_2$, with the following layer structure: ITO/NPB (30 nm)/Ga$_2$(saph)$_2$q$_2$:DCJTB(2%; 40 nm)/Ga$_2$(saph)$_2$q$_2$(15 nm)/Mg:Ag(10:1).
Figure 6:
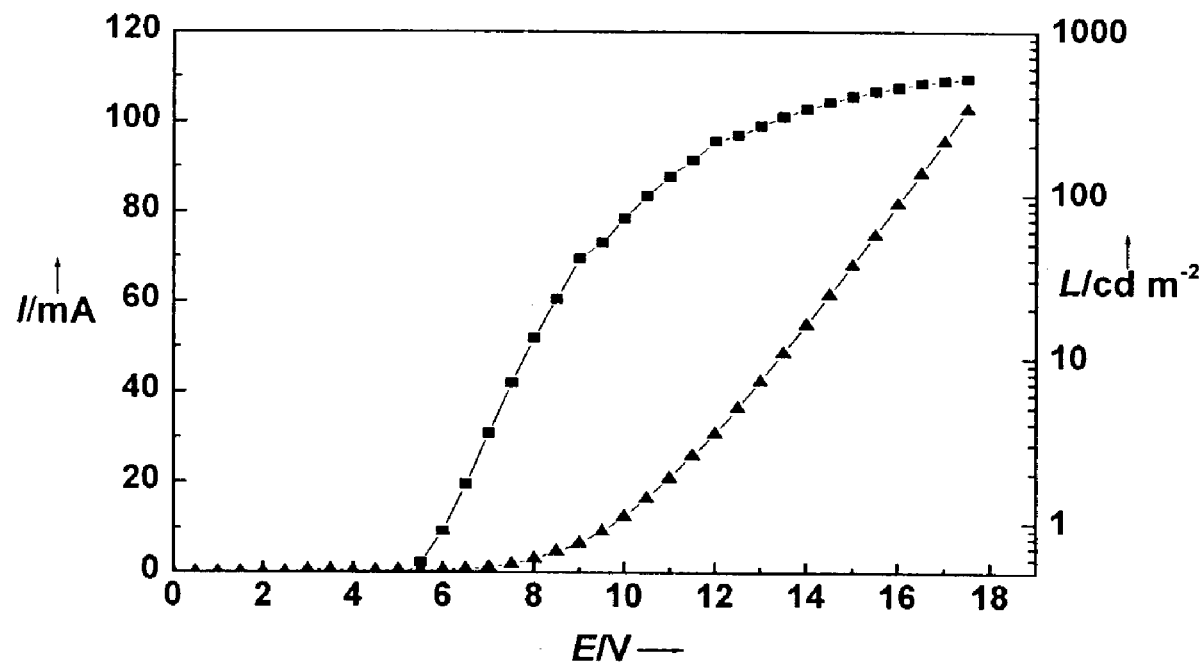
FIG. 6 is Current-voltage (triangle) and luminance-voltage (square) characteristics of the device: ITO/PEDOT: PSS/(Al(saph)DPM)$_2$:rubrene(1%)/Mg:Ag.
Figure 7:
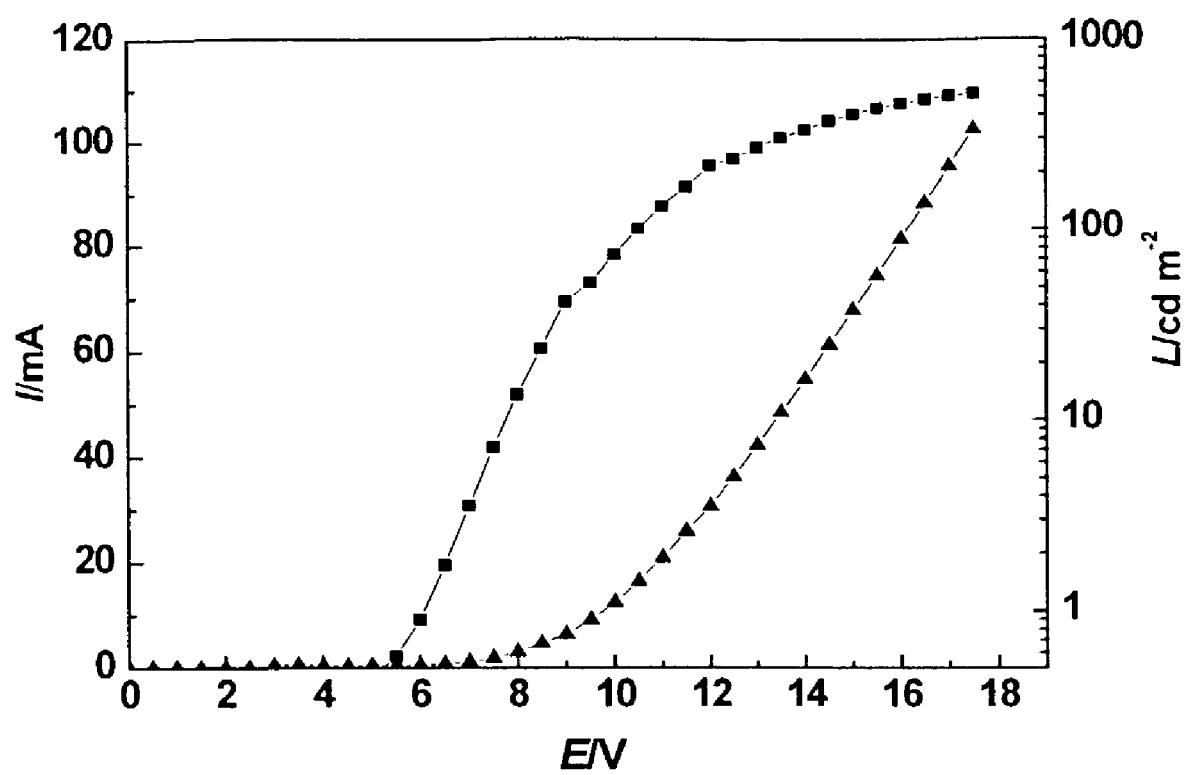
FIG. 7 is Current-voltage (triangle) and luminance-voltage (square) characteristics of the device: ITO/PEDOT: PSS/(Al(saph)DPM)$_2$:rubrene(1%)/Ca:Ag.

The configurations of devices 300 and 200 are similar, except that an additional hole-injection layer 306 is introduced in device 300 to assist hole injection from the anode. In FIG. 3, the numerals represent respectively: 304 anode; 306 hole-injection layer; 308 hole-transport layer; 310 luminescent layer; 312 electron-transport layer; 314 cathode; 316 organic EL medium. In this respect, the functions of the individual organic layers are distinct and can therefore be optimized independently.

The substrates for the EL devices 100, 200, and 300 are electrically insulating and light transparent. The light transparent property is desirable for viewing the EL emission through the substrate. For applications where the EL emission is viewed through the top electrode, the transmissive characteristic of the support is immaterial, and therefore, any appropriate substrate such as opaque semiconductor or ceramic wafers can be used. Of course, it is necessary to provide in these device configurations a light transparent top electrode.

The hole transporting layer of the organic EL device contains at least one hole-transporting aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monarylamine, diarylamine, triarylamine, or a polymeric arylamine.

Illustrations of useful hole-transport compounds are the following:
N,N'-bis(3-methylphenyl)-N,N'-bis(phenyl)-benzidine (TPD); ,N'-bis(4-methylphenyl)-N,N'-bis(phenyl)-benzidine(NPB); N,N'-Di(napthalene-2-yl)-N,N'-diphenylbenzidine); 1,3,5-Tris(3-methyldiphenylamino)benzene(m-MTDATA).

The luminescent layer of the organic EL medium comprises of a luminescent or fluorescent material where electroluminescence is produced as a result of electron-hole pair recombination in this region. In the simplest construction, the luminescent layer comprises of a single component, that is a pure material with a high fluorescent efficiency. A well-known material is tris (8-quinolinato) aluminum, (Alq$_3$), which produces excellent green electroluminescence. A preferred embodiment of the luminescent layer comprises a multi-component material consisting of a host material doped with one or more components of fluorescent dyes. Using this method, highly efficient EL devices can be constructed. Simultaneously, the color of the EL devices can be tuned by using fluorescent dyes of different emission wavelengths in a common host material. This dopant scheme has been described in considerable details for EL devices using Alq$_3$ as the host material by Tang et al. Applied Physics, Vol. 65, Pages 3610–3616, 1989; and U.S. Pat. No. 4,769,292.

An important relationship for choosing a fluorescent dye as a dopant capable of modifying the hue of light emission when present in a host material is a comparison of their bandgap potential which is defined as the energy difference between the highest occupied molecular orbital and the lowest unoccupied molecular orbital of the molecule. For efficient energy transfer from the host to the dopant molecule, a necessary condition is that the bandgap of the dopant is smaller than that of the host material. An advantage of using a blue host such as benzazole is that its bandgap is sufficiently large to effect energy transfer to a range of commonly available fluorescent dyes emitting in the blue. These blue dopants include coumarins, stilbenes, distyrylstilbenes, derivatives of anthracene, tetracene, perylene, and other conjugated benzenoids. Other dopants for EL emissions at longer wavelengths include coumarins, rhodamines and other green or red emitting fluorescent dyes.

In the practice of the present invention, the host material for forming the EL luminescent layer where light is emitted in response to electron-hole recombination includes a organometallic complex or a mixture of these organometallic complexes represented by formula (1). The dopants for the organometallic complexes may include fluorescent dyes as described above.

The above preferred materials for the multi-layers of the organic EL medium are each capable of film-forming—that is, capable of being fabricated as a continuous layer having a thickness of less than 5000 Å. A preferred method for forming the organic EL medium is vacuum vapor deposition. Extremely thin defect-free continuous layers can be formed by this method. Specifically, the individual layer thickness as low as about 50 Å can be constructed while still realizing satisfactory EL device performance. It is generally preferred that the overall thickness of the organic EL medium be at least about 1000 Å.

Other methods for forming thin films in EL devices of this invention include spin-coating from a solution containing the EL material. A combination of spin-coating method and vacuum vapor deposition method is also useful for the fabrication of multi-layer EL devices.

The anode and cathode of the organic EL device can each take any convenient conventional form. Where it is intended to transmit light from the organic EL device through the anode, this can be conveniently achieved by coating a thin conductive layer onto a light transparent substrate—e.g., a transparent or substantially transparent glass plate or plastic film.

In accordance with the present invention, a series of organic metal complexes for organic EL are disclosed as shown in Formula (1), which have variable tridentate ligands and bidentate ligands.

$$(L^2L^3M)_n \quad (1)$$

wherein: n is an integer of 1 or 2; M is trivalent metal selected from the group consisting of Al, Ga, In, Tl, and Ir and $L^2$ is a bidentate ligand, which has at least one coordinate atom of oxygen and is characterized as Formulae (2-1 and 2-2). When $L^2$ has one oxygen and one nitrogen atoms to coordinate the central ion, it can be characterized as Formula (2-1):

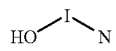
(2-1)

When $L^2$ has two oxygen atoms to coordinate the central ion, it can be characterized as formula

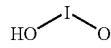
(2-2)

$L^3$ is a tridentate ligand with three chelate points as shown in Formula (3), in which X, Y independently represent CH or N. II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

(3)

When: X=CH, Y=N, $L^3$ has a structure characterized as Formula (3-1).

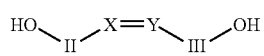
(3-1)

When: X=Y=CH, $L^3$ has a structure characterized as Formula (3-2).

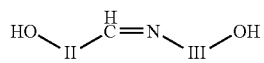
(3-2)

When: X=Y=N, $L^3$ has a structure characterized as Formula (3-3).

(3-3)

HO\_II\_N=N\_III\_OH

The following groups of molecular structures constitute specific examples of preferred organic metallic complex satisfying the requirement of the invention. However, the present invention is not limited to these metallic complexes.

Group I–Group III

Wherein:

$L^2$ is bidentate ligand as characterized as Formula (2-1), which can be selected from the group consisting of unsubstantiated or substituted 8-hydroxyquinoline, 2-(o-hydroxyphenyl)-benzoxazole, 4-hydroxy-1,5-naphthyridine, 5-hydroxyquinoxaline, 2-(o-hydroxylphenyl)-benzimidazole, 2-(o-hydroxylphenyl)-benzothiazole, 10-hydroxyl-benzoquinoline, 2-carboxyl-pyridine. The substituent groups can be alkyl having 1–8 carbon atoms, halogen, cyano, amino, amido, sulfonyl, carbonyl, aryl, or heteroalkyl groups. The typical structures of $L^2$ as the following:

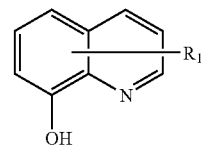
$L^2$-I

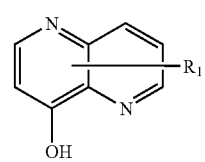
$L^2$-II

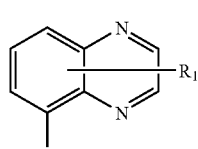
$L^2$-III

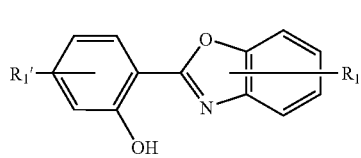
$L^2$-IV

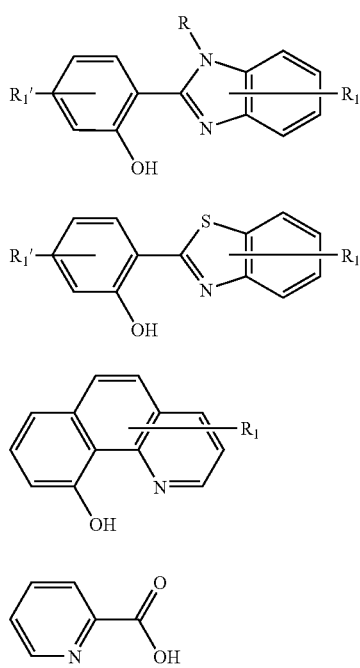

L²-V

L²-VI

L²-VII

L²-VIII

Group I

L³ is a tridentate ligand as shown in Formula (3-1), II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

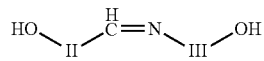

(3-1)

n is an integer of 1 or 2;
M is a trivalent metal selected from the group consisting of Ga, In, Tl, and Ir.

Group II

L³ is a tridentate ligand as shown in Formula (3-2), II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

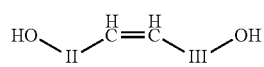

(3-2)

n is an integer of 1 or 2;
M is a trivalent metal selected from the group consisting of Ga, In, Tl, and Ir.

Group III

L³ is a tridentate ligand as shown in Formula (3-3), II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

(3-3)

n is an integer of 1 or 2;
M is a trivalent metal selected from the group consisting of Ga, In, Tl, and Ir.

Typical complexes of the group I-III were shown in below table 1.

TABLE 1 typical complexes of the group I–III

| Complex No. | M | n | L² 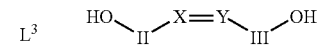 | L³ 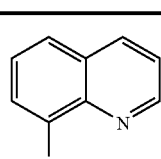 | | | |
|---|---|---|---|---|---|---|---|
| | | | | II | III | X | Y |
| I-1 | Ga | 2 | 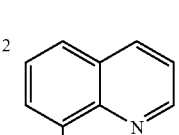 | phenyl | phenyl | CH | N |
| I-2 | Ga | 2 | 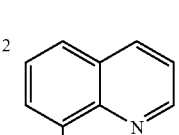 | 2-hydroxy-1-naphthaldehyde | phenyl | CH | N |

TABLE 1-continued typical complexes of the group I–III $L^3$ HO—II—X=Y—III—OH

| Complex No. | M | n | $L^2$ HO—I—N | II | III | X | Y |
|---|---|---|---|---|---|---|---|
| I-3 | In | 1 | 8-hydroxyquinoline | phenyl | phenyl | CH | N |
| I-4 | Ga | 2 | 8-hydroxyquinoline | phenyl | 3-amino-2-naphthol | CH | N |
| I-5 | Al | 2 | 4-methyl-8-hydroxyquinoline | phenyl | phenyl | CH | N |
| I-6 | Ga | 2 | 5-fluoro-8-hydroxyquinoline | phenyl | phenyl | CH | N |
| I-7 | Ga | 2 | 2-(2-hydroxyphenyl)benzoxazole | phenyl | phenyl | CH | N |
| I-8 | Al | 1 | 2-(2-hydroxyphenyl)benzoxazole | 2-hydroxy-1-naphthaldehyde | phenyl | CH | N |
| I-9 | Ga | 2 | 8-hydroxy-1,5-naphthyridine | phenyl | phenyl | CH | N |
| I-10 | Al | 1 | 8-hydroxy-1,5-naphthyridine | phenyl | phenyl | CH | N |

TABLE 1-continued
typical complexes of the group I–III
| Complex No. | M | n | L² | L³ II | III | X | Y |
|---|---|---|---|---|---|---|---|
| I-11 | Ir | 1 | 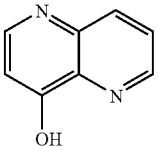 | phenyl | phenyl | CH | N |
| I-12 | Ga | 2 | 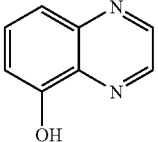 | phenyl | phenyl | CH | N |
| I-13 | Al | 1 | 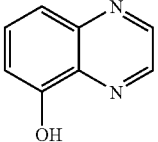 | phenyl | phenyl | CH | N |
| I-14 | Ga | 2 | 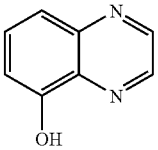 | 2-hydroxy-1-naphthaldehyde | phenyl | CH | N |
| I-15 | Ga | 2 | 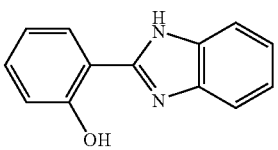 | phenyl | phenyl | CH | N |
| I-16 | Al | 1 | 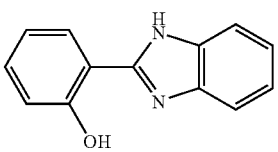 | phenyl | phenyl | CH | N |
| I-17 | In | 1 | 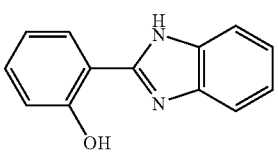 | 2-hydroxy-1-naphthaldehyde | phenyl | CH | N |
| I-18 | Ga | 2 | 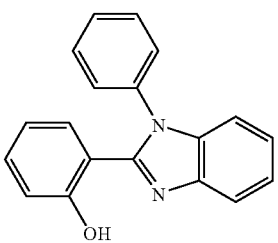 | phenyl | phenyl | CH | N |

TABLE 1-continued typical complexes of the group I–III

| Complex No. | M | n | L² | L³ II | III | X | Y |
|---|---|---|---|---|---|---|---|
| I-19 | Ga | 2 | 2-(benzothiazol-2-yl)phenol | phenyl | phenyl | CH | N |
| I-20 | Al | 2 | 2-(benzothiazol-2-yl)phenol | phenyl | phenyl | CH | N |
| I-21 | Ga | 1 | 10-hydroxybenzo[h]quinoline | phenyl | phenyl | CH | N |
| I-22 | Ga | 2 | pyridine-2-carboxylic acid | phenyl | phenyl | CH | N |
| II-1 | Ga | 2 | 8-hydroxyquinoline | phenyl | phenyl | CH | CH |
| II-2 | Ga | 2 | 8-hydroxyquinoline | 2-hydroxy-1-naphthaldehyde | phenyl | CH | CH |
| II-3 | Al | 1 | 8-hydroxyquinoline | Phenyl | phenyl | CH | CH |
| II-4 | Ga | 2 | 4-methyl-8-hydroxyquinoline | phenyl | phenyl | CH | CH |

TABLE 1-continued typical complexes of the group I–III

| Complex No. | M | n | L² | L³ II | III | X | Y |
|---|---|---|---|---|---|---|---|
| II-5 | Tl | 1 | 4-methyl-8-hydroxyquinoline | phenyl | phenyl | CH | CH |
| II-6 | Ga | 2 | 5-fluoro-8-hydroxyquinoline | phenyl | phenyl | CH | CH |
| II-7 | Ir | 1 | 5-fluoro-8-hydroxyquinoline | phenyl | phenyl | CH | CH |
| II-8 | Ga | 2 | 2-(2-hydroxyphenyl)benzoxazole | phenyl | phenyl | CH | CH |
| II-9 | Ga | 2 | 2-(2-hydroxyphenyl)benzoxazole | phenyl | 2-hydroxy-1-naphthaldehyde | CH | CH |
| II-10 | Ga | 2 | 8-hydroxy-1,5-naphthyridine | phenyl | phenyl | CH | CH |
| II-11 | In | 2 | 8-hydroxyquinoxaline | phenyl | phenyl | CH | CH |
| II-12 | Ga | 2 | 8-hydroxyquinoxaline | phenyl | 2-hydroxy-1-naphthaldehyde | CH | CH |

TABLE 1-continued
typical complexes of the group I–III
| Complex No. | M | n | L² | L³ HO—II—X=Y—III—OH | | | |
|---|---|---|---|---|---|---|---|
| | | | HO—I—N | II | III | X | Y |
| II-13 | Ga | 2 |  | phenyl | phenyl | CH | CH |
| II-14 | Ir | 1 | 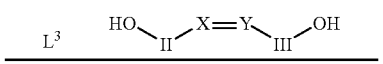 | phenyl | 2-hydroxy-1-naphthaldehyde | CH | CH |
| II-15 | Ga | 2 | 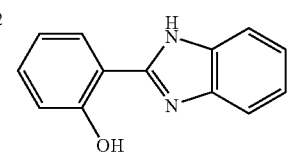 | phenyl | phenyl | CH | CH |
| II-16 | Ga | 2 | 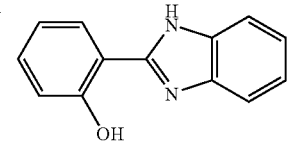 | phenyl | phenyl | CH | CH |
| II-17 | Ga | 1 | 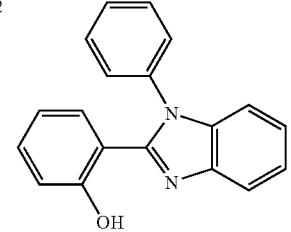 | phenyl | phenyl | CH | CH |
| II-18 | Ga | 2 | 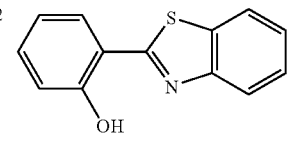 | phenyl | phenyl | CH | CH |
| III-1 | Ga | 2 | 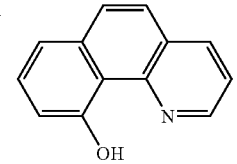 | phenyl | phenyl | N | N |
| III-2 | Ga | 2 | 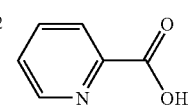 | naphthyl | phenyl | N | N |

TABLE 1-continued typical complexes of the group I–III

| Complex No. | M | n | L² | L³ II | III | X | Y |
|---|---|---|---|---|---|---|---|
| III-3 | Al | 2 | 4-methyl-8-hydroxyquinoline | phenyl | phenyl | N | N |
| III-4 | Tl | 1 | 4-methyl-8-hydroxyquinoline | phenyl | phenyl | N | N |
| III-5 | Ga | 2 | 5-fluoro-8-hydroxyquinoline | phenyl | phenyl | N | N |
| III-6 | Ga | 2 | 2-(2-hydroxyphenyl)benzoxazole | phenyl | phenyl | N | N |
| III-7 | Ga | 2 | 2-(2-hydroxyphenyl)benzoxazole | phenyl | naphthyl | N | N |
| III-8 | Ir | 1 | 4-hydroxy-1,5-naphthyridine | phenyl | phenyl | N | N |
| III-9 | Ga | 2 | 8-hydroxy-1,5-naphthyridine | phenyl | naphthyl | N | N |
| III-10 | Ga | 2 | 8-hydroxyquinoxaline | phenyl | phenyl | N | N |

TABLE 1-continued typical complexes of the group I–III

| Complex No. | M | n | L² HO-I-N | L³ II | HO-II-X=Y-III-OH III | X | Y |
|---|---|---|---|---|---|---|---|
| III-11 | In | 1 | (8-hydroxyquinoxaline) | phenyl | naphthyl | N | N |
| III-12 | Ga | 2 | (2-(2-hydroxyphenyl)benzimidazole) | phenyl | phenyl | N | N |
| III-13 | Al | 1 | (2-(2-hydroxyphenyl)benzimidazole) | phenyl | naphthyl | N | N |
| III-14 | Ga | 2 | (2-(2-hydroxyphenyl)-1-phenylbenzimidazole) | phenyl | phenyl | N | N |
| III-15 | Ga | 2 | (2-(2-hydroxyphenyl)benzothiazole) | phenyl | phenyl | N | N |
| III-16 | Ga | 1 | (10-hydroxybenzo[h]quinoline) | phenyl | phenyl | N | N |
| III-17 | Ga | 2 | (picolinic acid) | phenyl | phenyl | N | N |

According to the definitions in table 1, it is obvious that some Complexes have the following constitutional structures respectively.
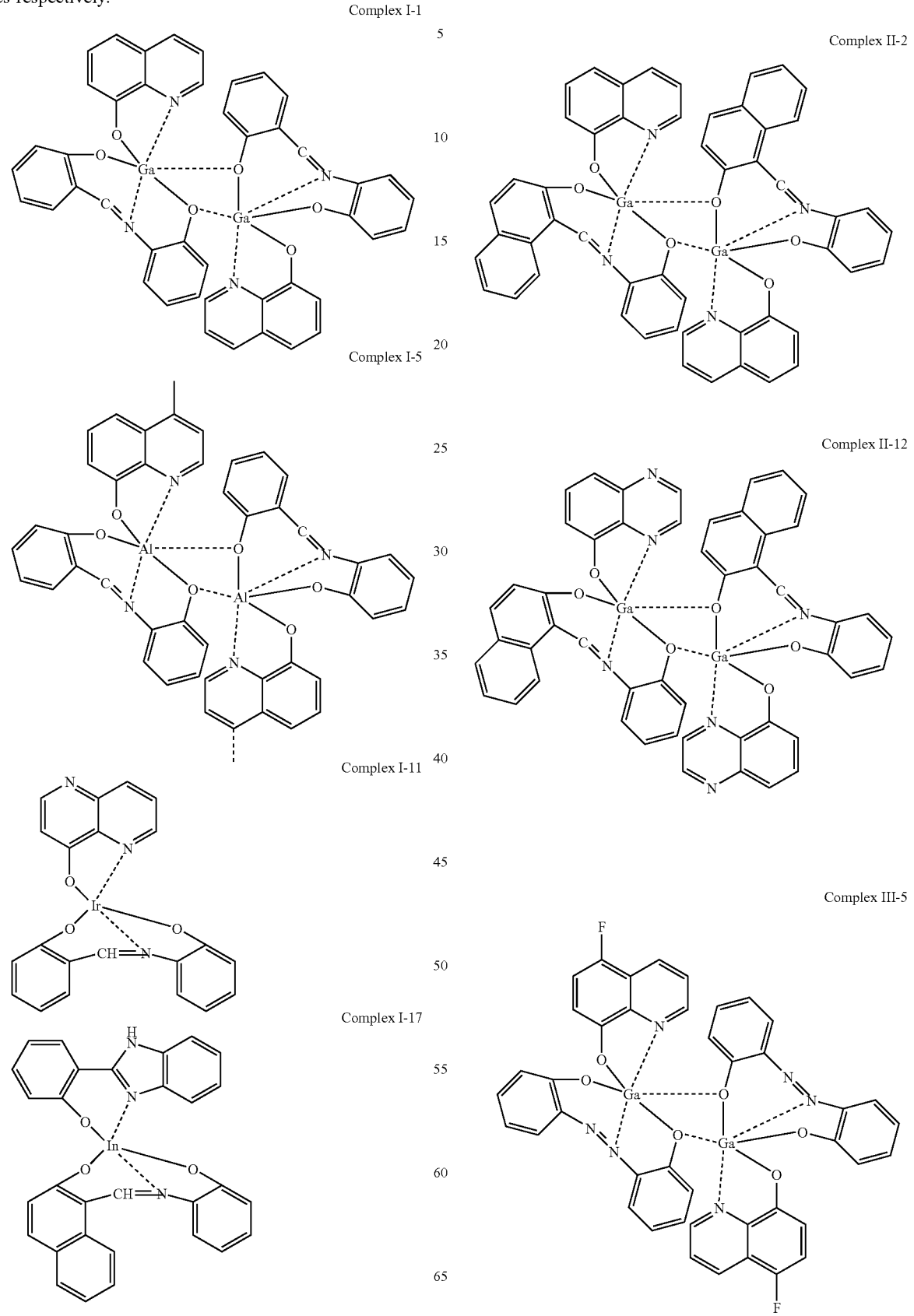

Complex III-4

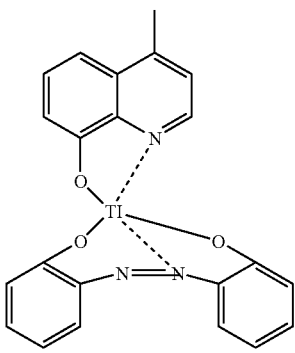

Group IV–Group VI

Wherein:

$L^2$ is bidentate ligand which could give two oxygen atoms to coordinate the central ions. As characterized as Formula (2-2), $L^2$ can be unsubstituted or substituted β-diketone, or modified β-diketone, or o-hydroxyl-arylketone.

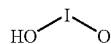 (2-2)

The typical structures of $L^2$ as the following, in which $R^1$, $R^2$, $R^3$, $R^4$, $R^5$, $R^6$, $R^7$, and $R^8$ are individually hydrogen, an alkyl or haloalkyl group having 1–18 carbon atoms, halogen, cyano, amino, amido, sulfonyl, carbonyl, and 5–24 atoms necessary to complete a fused aromatic ring.

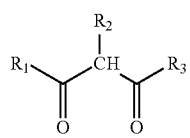 $L^2$-IX

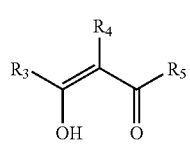 $L^2$-X

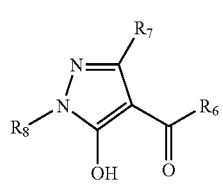 $L^2$-XI

Group IV $L^3$ is a tridentate ligand as shown in Formula (3-1), wherein II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

 (3-1)

n is an integer of 1 or 2;

M is a trivalent metal selected from the group consisting of Ga, In, Tl, and Ir.

Group V $L^3$ is a tridentate ligand as shown in Formula (3-2), wherein II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

 (3-2)

n is an integer of 1 or 2;

M is a trivalent metal selected from the group consisting of Ga, In, Tl, and Ir.

Group VI $L^3$ is a tridentate ligand as shown in Formula (3-3), wherein II, III are unsubstituted or substituted aryl or heteroalkyl groups. The substituent groups can be alkyl having 1–8 carbon atoms, halogen, cyano, amino, amido, sulfonyl, carbonyl, aryl, or heteroalkyl groups such as furan, thiophene, pyrrole, and pyridine.

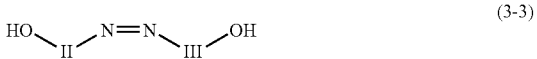 (3-3)

n is an integer of 1 or 2;

M is a trivalent metal selected from the group consisting of Ga, In, Tl, and Ir.

Typical complexes of the group IV-VI were shown in below table 2.

TABLE 2 typical complexes of the group IV–VI.

$L^3$: HO—II—X=Y—III—OH

| Complex No. | M | n | $L^2$ (HO—I—N) | II | III | X | Y |
|---|---|---|---|---|---|---|---|
| IV-1 | Al | 2 | acetylacetonate (pentane-2,4-dione) | phenyl | phenyl | CH | N |
| IV-2 | Ga | 2 | acetylacetonate | phenyl | phenyl | CH | N |
| IV-3 | Ga | 2 | acetylacetonate | 2-hydroxy-1-naphthaldehyde | phenyl | CH | N |
| IV-4 | In | 1 | acetylacetonate | phenyl | 3-amino-2-naphthol | CH | N |
| IV-5 | Al | 2 | 2,2-dimethyl-hexane-3,5-dione | phenyl | phenyl | CH | N |
| IV-6 | Al | 2 | 2-methyl-hexane-3,5-dione | phenyl | phenyl | CH | N |
| IV-7 | Ga | 2 | 2-methyl-hexane-3,5-dione | phenyl | phenyl | CH | N |
| IV-8 | Al | 2 | 2,2,6,6-tetramethyl-heptane-3,5-dione | phenyl | phenyl | CH | N |
| IV-9 | Ga | 2 | 1,1,1-trifluoro-5,5-dimethyl-hexane-2,4-dione | phenyl | phenyl | CH | N |
| IV-10 | Ga | 2 | 1-phenyl-4,4-dimethyl-pentane-1,3-dione | phenyl | phenyl | CH | N |
| IV-11 | Al | 2 | 4,4,4-trifluoro-1-phenyl-butane-1,3-dione | phenyl | phenyl | CH | N |

TABLE 2-continued typical complexes of the group IV–VI.

| Complex No. | M | n | L² | II | III | X | Y |
|---|---|---|---|---|---|---|---|
| IV-12 | Al | 2 | dibenzoylmethane | phenyl | phenyl | CH | N |
| IV-13 | Ga | 2 | 1-(naphthalen-2-yl)-3-(4-dimethylaminophenyl)propane-1,3-dione | phenyl | phenyl | CH | N |
| IV-14 | Al | 2 | 4,4,4-trifluoro-1-(thiophen-2-yl)butane-1,3-dione | phenyl | phenyl | CH | N |
| IV-15 | In | 1 | 4,4,4-trifluoro-1-(thiophen-2-yl)butane-1,3-dione | phenyl | phenyl | CH | N |
| IV-16 | Ga | 2 | 4,4,4-trifluoro-1-(furan-2-yl)butane-1,3-dione | phenyl | phenyl | CH | N |
| IV-17 | Al | 2 | 4,4,4-trifluoro-1-(furan-2-yl)butane-1,3-dione | phenyl | phenyl | CH | N |
| IV-18 | Ga | 2 | 1-phenyl-3-(thiophen-2-yl)propane-1,3-dione | phenyl | phenyl | CH | N |
| IV-19 | Ir | 1 | 1-phenyl-3-(furan-2-yl)propane-1,3-dione | phenyl | phenyl | CH | N |

TABLE 2-continued typical complexes of the group IV–VI.

| Complex No. | M | n | L² | L³ II | III | X | Y |
|---|---|---|---|---|---|---|---|
| IV-20 | Ga | 2 | 1,3-di(2-thienyl)-1,3-propanedione | phenyl | phenyl | CH | N |
| IV-21 | Al | 1 | 3-(9-anthracenylmethyl)-2,4-pentanedione | phenyl | phenyl | CH | N |
| IV-22 | Al | 1 | 1-(5-hydroxy-3-methyl-1-phenyl-1H-pyrazol-4-yl)ethanone | phenyl | phenyl | CH | N |
| IV-23 | Al | 1 | (5-hydroxy-3-methyl-1-phenyl-1H-pyrazol-4-yl)(phenyl)methanone | phenyl | phenyl | CH | N |
| IV-24 | Ga | 1 | 1-(5-hydroxy-3-methyl-1-phenyl-1H-pyrazol-4-yl)-2,2-dimethylpropan-1-one | phenyl | phenyl | CH | N |
| IV-25 | Al | 1 | 2'-hydroxyacetophenone | phenyl | phenyl | CH | N |
| IV-26 | Al | 2 | 2'-hydroxy-4'-(trifluoromethyl)acetophenone | phenyl | phenyl | CH | N |
| V-1 | Al | 2 | 2,4-pentanedione | phenyl | phenyl | CH | CH |

TABLE 2-continued
typical complexes of the group IV–VI.
| Complex No. | M | n | L² HO—I—N | L³ HO—II—X=Y—III—OH | | | |
|---|---|---|---|---|---|---|---|
| | | | | II | III | X | Y |
| V-2 | Ga | 2 | 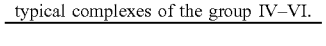 | 2-hydroxy-1-naphthaldehyde | Phenyl | CH | CH |
| V-3 | In | 1 | 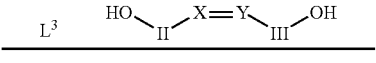 | phenyl | 3-amino-2-naphthol | CH | CH |
| V-4 | Al | 2 | 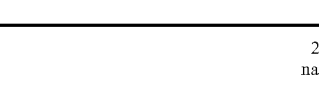 | phenyl | phenyl | CH | CH |
| V-5 | Al | 2 |  | phenyl | phenyl | CH | CH |
| V-6 | Tl | 1 |  | phenyl | phenyl | CH | CH |
| V-7 | Al | 2 |  | phenyl | phenyl | CH | CH |
| V-8 | Al | 2 |  | phenyl | phenyl | CH | CH |
| V-9 | Al | 2 |  | phenyl | phenyl | CH | CH |
| V-10 | Ga | 2 |  | phenyl | phenyl | CH | CH |
| V-11 | Al | 2 |  | phenyl | phenyl | CH | CH |

TABLE 2-continued typical complexes of the group IV–VI.

| Complex No. | M | n | L² (HO—I—N) | L³ II | III | X | Y |
|---|---|---|---|---|---|---|---|
| V-12 | In | 1 | 1,3-diphenyl-1,3-propanedione | phenyl | phenyl | CH | CH |
| V-13 | Al | 2 | 1-(naphthalen-2-yl)-3-(4-dimethylaminophenyl)-1,3-propanedione | phenyl | phenyl | CH | CH |
| V-14 | Al | 2 | 1-(thiophen-2-yl)-4,4,4-trifluoro-1,3-butanedione | phenyl | phenyl | CH | CH |
| V-15 | Al | 2 | 1-(furan-2-yl)-4,4,4-trifluoro-1,3-butanedione | phenyl | phenyl | CH | CH |
| V-16 | Al | 2 | 1-phenyl-3-(thiophen-2-yl)-1,3-propanedione | phenyl | phenyl | CH | CH |
| V-17 | In | 1 | 1-phenyl-3-(furan-2-yl)-1,3-propanedione | phenyl | phenyl | CH | CH |
| V-18 | Al | 2 | 1,3-di(thiophen-2-yl)-1,3-propanedione | phenyl | phenyl | CH | CH |
| V-19 | Al | 1 | 3-(anthracen-9-ylmethyl)-2,4-pentanedione | phenyl | phenyl | CH | CH |

TABLE 2-continued typical complexes of the group IV–VI.

| Complex No. | M | n | L² | L³ | | | |
|---|---|---|---|---|---|---|---|
| | | | | II | III | X | Y |
| V-20 | Ga | 1 | (9-anthracenylmethyl)-substituted acetylacetonate | phenyl | phenyl | CH | CH |
| V-21 | Al | 1 | 4-acetyl-3-methyl-1-phenyl-5-hydroxypyrazole | phenyl | phenyl | CH | CH |
| V-22 | Al | 1 | 4-benzoyl-3-methyl-1-phenyl-5-hydroxypyrazole | phenyl | phenyl | CH | CH |
| V-23 | Al | 1 | 3-methyl-1-phenyl-4-(trifluoroacetyl)-5-hydroxypyrazole | phenyl | phenyl | CH | CH |
| V-24 | Ga | 1 | 2′-hydroxyacetophenone | phenyl | phenyl | CH | CH |
| V-25 | Al | 2 | 2′-hydroxy-4′-(trifluoromethyl)acetophenone | phenyl | phenyl | CH | CH |
| VI-1 | Al | 2 | acetylacetonate | phenyl | phenyl | N | N |
| VI-2 | Ga | 2 | acetylacetonate | 2-hydroxy-1-naphthaldehyde | Phenyl | N | N |
| VI-3 | In | 1 | acetylacetonate | phenyl | 3-amino-2-naphthol | N | N |

TABLE 2-continued typical complexes of the group IV–VI.

| Complex No. | M | n | L² | L³ | | | |
|---|---|---|---|---|---|---|---|
| | | | | II | III | X | Y |
| VI-4 | Al | 2 | (2,2-dimethyl-pentane-2,4-dione) | phenyl | phenyl | N | N |
| VI-5 | Al | 2 | (5-methyl-hexane-2,4-dione) | phenyl | phenyl | N | N |
| VI-6 | Al | 2 | (6-methyl-heptane-2,4-dione) | phenyl | phenyl | N | N |
| VI-7 | Al | 2 | (2,2,6,6-tetramethyl-heptane-3,5-dione) | phenyl | phenyl | N | N |
| VI-8 | Ga | 2 | (1,1,1-trifluoro-5,5-dimethyl-hexane-2,4-dione) | phenyl | phenyl | N | N |
| VI-9 | Ga | 2 | (1-phenyl-4,4-dimethyl-pentane-1,3-dione) | phenyl | phenyl | N | N |
| VI-10 | Al | 2 | (4,4,4-trifluoro-1-phenyl-butane-1,3-dione) | phenyl | phenyl | N | N |
| VI-11 | Al | 2 | (1,3-diphenyl-propane-1,3-dione) | phenyl | phenyl | N | N |
| VI-12 | Al | 2 | (1-(naphth-2-yl)-3-(4-dimethylaminophenyl)-propane-1,3-dione) | phenyl | phenyl | N | N |

TABLE 2-continued
typical complexes of the group IV–VI.
| Complex No. | M | n | L² | II | III | X | Y |
|---|---|---|---|---|---|---|---|
| VI-13 | Al | 2 | 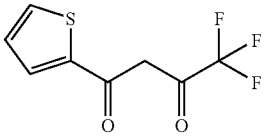 | phenyl | phenyl | N | N |
| VI-14 | Al | 2 | 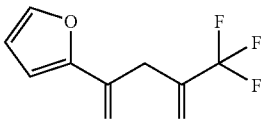 | phenyl | phenyl | N | N |
| VI-15 | Ga | 1 | 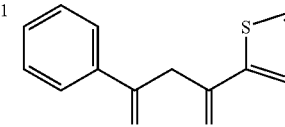 | phenyl | phenyl | N | N |
| VI-16 | Ir | 1 | 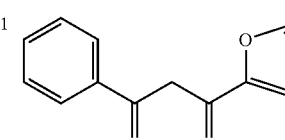 | phenyl | phenyl | N | N |
| VI-17 | Al | 2 | 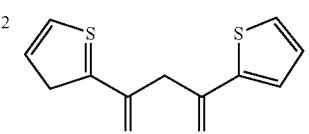 | phenyl | phenyl | N | N |
| VI-18 | Al | 1 | 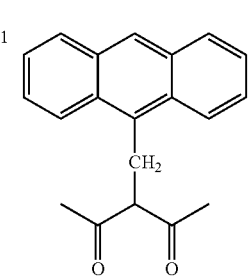 | phenyl | phenyl | N | N |
| VI-19 | Al | 1 | 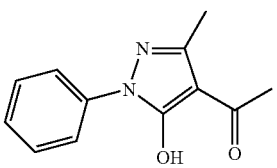 | phenyl | phenyl | N | N |
| VI-20 | Ga | 1 | 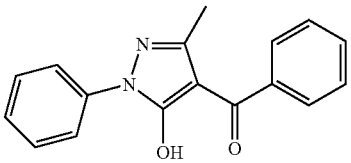 | phenyl | phenyl | N | N |

TABLE 2-continued
typical complexes of the group IV–VI.
| Complex No. | M | n | L²  | L³  | | | |
|---|---|---|---|---|---|---|---|
| | | | | II | III | X | Y |
| VI-21 | Al | 1 |  | phenyl | phenyl | N | N |
| VI-22 | Al | 2 |  | phenyl | phenyl | N | N |
| VI-23 | Al | 2 |  | phenyl | phenyl | N | N |
According to the definitions in table 2, it is obvious that some Complexes have the following constitutional structures respectively.
Complex IV-2
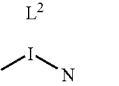
Complex IV-14
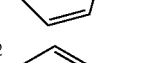
Complex V-4
Complex V-19
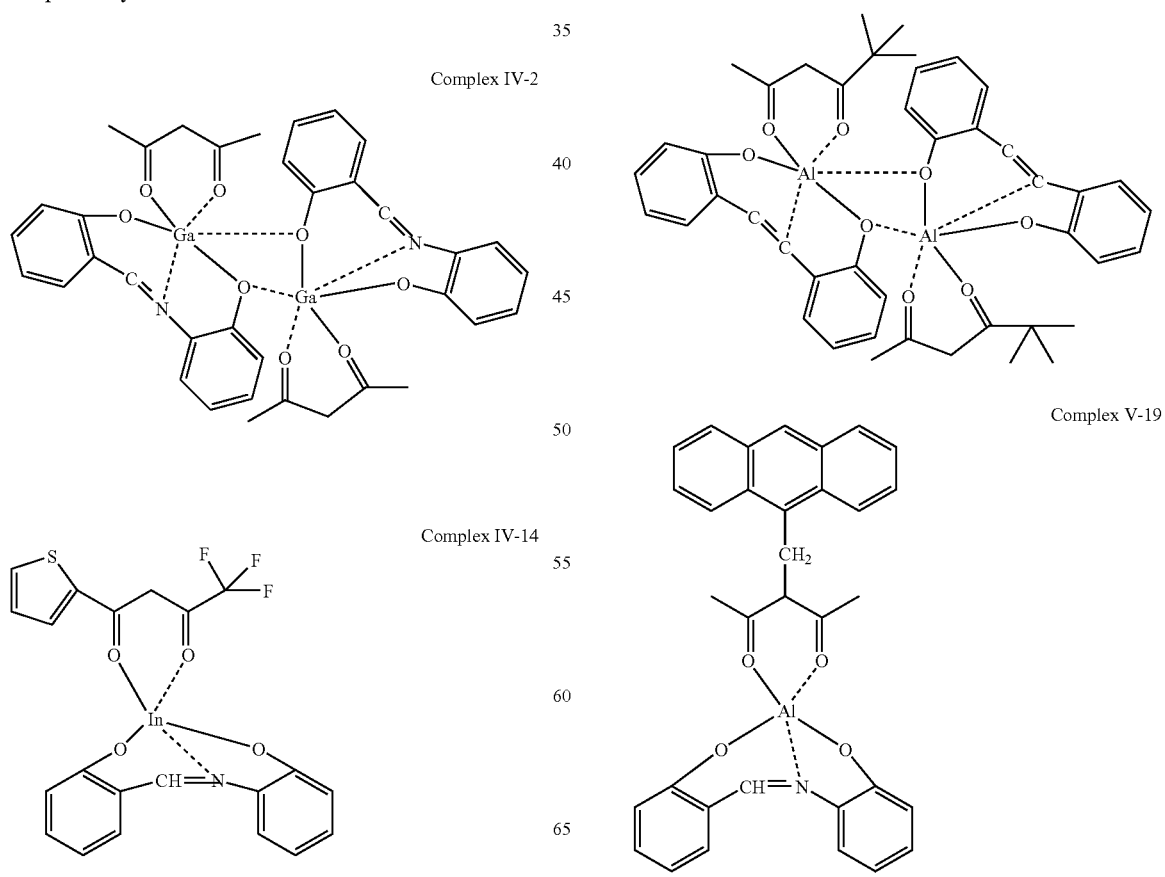

-continued

Complex VI-2

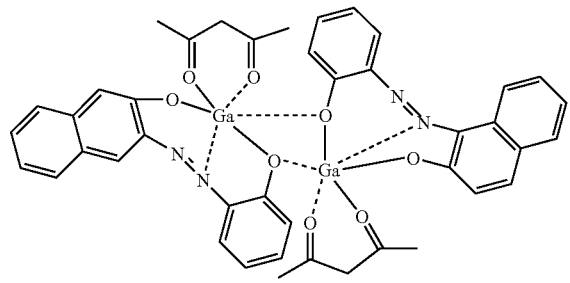

Complex VI-10

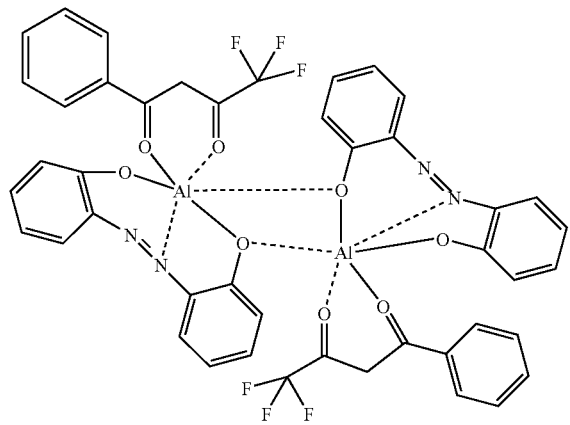

All the above these compounds can be prepared by the following two steps: the first step is the synthesis of the tridentate ligands, the second step is the synthesis of the objective complexes.

The first step is the synthesis of the tridentate ligands. The ligands described in Formula (3-1), are shiff bases, which can be synthesized by conventional shiff base synthesis methods comprising the steps: heating the mixture of o-hydroxy-aryl aldehyde and o-hydroxy-aryl alcohol and recrystallization in an organic solvent. The ligands described in Formula(3-2) can be synthesized by the method of stilbene (New Journal of chemistry, 25(5), 2001; Bull Soc. Chim. FR. 958,1967). The ligands described in Formula (3-3) can be synthesized by the method of Willstatter (Anal. Chem., 35, 1144).

The second step is the complexing reaction of metal ions and the two ligands. Inorganic metal (III) salts or organic metal (III) compounds in solvent are added with the solution of ligands. The product was collected by filtration and washed with solvents. The complexes were further purified by the train sublimation method.

The advantage of these materials lies in their exceedingly high luminescent efficiencies and excellent film-forming capability. These materials have some unique characteristics that will be conducive to forming high quality amorphous films. Such novel complexes can be used as a thermal stable emitting material for OLEDs. In addition, a series of emitting colors have been obtained from these materials including green, yellow, and red, some of which are remained rare now. Especially as the host material of red dopants, the color position in the color coordinates system shows strong potential as a red light-emitting material for organic electroluminescence. Moreover, these materials have high electron-transport mobility and can be used as charge carrier layer not only in OLEDs but also in other organic optoelectronic technologies. From the viewpoint of molecular design, the introductions of tridentate ligands in the complex structure open a new route for exploring new materials for organic EL, even for organic optoelectronics. By changing the tridentate ligands and central atoms, a novel class of materials, dimers of organometallic complexes have been obtained herein, which have some exceptional properties, such as much higher luminescent efficiency, better film forming capability. It is worthwhile to note that groups VI-VI complexes with diketone ligands have proven to exhibit extraordinary film-forming capability by solution processes as well as much higher luminescent efficiency than the typical Alq3.

The following non-limiting example further serves to illustrate the invention.

EXAMPLES

The invention and its advantages are further illustrated by the examples as follows:

Material Preparation

Example 1

Synthesis of bis[(8-hydroxyquinolino)(salicylidene-o-hydroxyanilino)gallium] (Complex I-1)

Complex I-1 was synthesized through a reaction in the ethanol solution of 8-hydroxyquinoline, salicylidene-o-aminophenol and $GaCl_3$ as follows. First, a solution of 8-hydroxyquinoline (0.05M) and piperidine (0.05M) in 20 ml ethanol was added to a solution of $GaCl_3$ (0.5M) in 10 ml ethanol very slowly with an intensive stirring. Then, a solution of salicylidene-o-aminophenol (0.01M) and piperidine (0.02M) in 50 ml ethanol was introduced slowly. The mixture was stirred for about 2 hour and cooled to room temperature and kept in dark for about 1 hour. An orange precipitate was formed when equivalent amount water was poured into the solution. The product was collected by filtration and washed with ethanol rapidly, then dried under an infrared lamp. The obtained product powder showed strong yellow fluorescence under an ultraviolet lamp. The materials were further purified by an improved train sublimation method. The salicylidene-o-aminophenol ligand was obtained by heating the mixture of 2-aminophenol and 2-hydroxy-salicylic aldehyde in ethanol solution and the following recrystallization. The molecular structure of Complex I-1 was supported by mass spectrum (MS), element analysis and a single-crystal X-ray diffraction analysis on the crystal selected from the sublimed product.

After drying, the bis[(8-hydroxyquinolino)(salicylidene-o-hydroxyanilino)gallium] was collected and weighed 3.61 g in a yield of 85%. MS found: m/e, 850.425; Element analysis found: C, 62.28%; H, 3.52%; N, 6.52%; O, 11.53%; Calc. for Complex I-1: C, 62.13%; H, 3.51%; N, 6.52%; O, 11.53%.

Example 2

Synthesis of bis[(8-hydroxyquinolino)(2-hydroxy-1-naphthylaldehyde-o-hydroxyanilino)gallium] (Complex I-2)

According to the synthesis procedures of Complex I-1, Complex I-2 was prepared by replacing 2-hydroxy-salicylic aldehyde with 2-hydroxy-1-naphthylaldehyde.

After drying, the bis[(8-hydroxyquinolino)(2-hydroxy-1-naphthylaldehyde-o-hydroxyanilino)gallium] was collected and weighed 3.71 g in a yield of 78%. MS:m/e, 950; 475, Element analysis found: C, 65.60%; H, 3.49%; N, 5.80%; Calc.: C, 65.68%; H, 3.58%; N, 5.89%.

Example 3

Synthesis of bis[(8-hydroxyquinolino)(salicylidene-2-hydroxyl-1-naphthylamine)gallium] (Complex I-4)

According to the synthesis procedures of Complex I-1, Complex I-3 was prepared by replacing 2-aninophenol with 2-hydroxyl-1-naphthylamine.

After drying, the bis[(8-hydroxyquinolino)(salicylidene-2-hydroxyl-1-naphthylamine)gallium] was collected and weighed 3.63 g in a yield of 76%. MS: m/e, 954,477, Element analysis found: C, 65.77; H, 3.65; N, 6.25; Calc.: C, 65.72; H, 3.61; N, 6.30.

Example 4

Synthesis of bis[(4-methyl-8-hydroxyquinolino)(salicylidene-o-hydroxyanilino)aluminum] (Complex I-5)

According to the synthesis procedures of Complex I-1, Complex I-5 was prepared by replacing 8-hydroxyquinoline with 4-methyl-8-hydroxyquinoline and $GaCl_3$ with $AlCl_3$.

After drying, the bis[(4-methyl-8-hydroxyquinolino)(salicylidene-o-hydroxyanilino)aluminum] was collected and weighed 3.42 g in a yield of 78%. MS: m/e, 793, Element analysis found: C, 69.46; H, 4.31; N, 6.92, Calc.: C, 69.56; H, 4.32; N, 6.98.

Example 5

Synthesis of bis[(5-fluoro-8-hydroxyquinolino)(salicylidene-o-hydroxyanilino)gallium] (Complex I-6)

According to the synthesis procedures of Complex I-1, Complex I-6 was prepared by replacing 8-hydroxyquinoline with 5-fluoro-8-hydroxyquinoline.

After drying, the bis[(5-fluoro-8-hydroxyquinolino)(salicylidene-o-hydroxyanilino)gallium] was collected and weighed 3.32 g in a yield of 75%. MS: m/e, 886, Element analysis found: C, 59.52; H, 4.32; N, 6.30; Calc.: C, 59.59; H, 4.29; N, 6.32.

Example 6

Synthesis of bis[(2-(o-hydroxyphenyl)-benzoxazole)(salicylidene-o-hydroxyanilino)gallium] (Complex I-7)

According to the synthesis procedures of Complex I-1, Complex I-7 was prepared by replacing 8-hydroxyquinoline with 2-(o-hydroxphenyl)-benzoxazole.

After drying, the bis[(2-(o-hydroxphenyl)-benzoxazole)(salicylidene-o-hydroxyanilino) gallium] was collected and weighed 3.83 g in a yield of 78%. MS:m/e; 982, Element analysis found: C, 63.39; H, 3.40; N, 5.62; Calc.: C, 63.41; H, 3.46; N, 5.69.

Example 7

Synthesis of bis[(4-hydroxy-1,5-naphthyridine)(salicylidene-o-hydroxyanilino)gallium] (Complex I-9)

According to the synthesis procedures of Complex I-1, Complex I-9 was prepared by replacing 8-hydroxyquinoline with 4-hydroxy-1,5-naphthyridine.

After drying, the bis[(4-hydroxy-1,5-naphthyridine)(salicylidene-o-hydroxyanilino)gallium] was collected and weighed 3.24 g in a yield of 76%. MS:m/e, 852, Element analysis found: C, 59.10; H, 3.20; N, 9.81; Calc.: C, 59.15; H, 3.29; N, 9.86.

Example 8

Synthesis of [(4-hydroxy-1,5-naphthyridine)(salicylidene-o-hydroxyanilino)aluminum] (Complex I-10)

According to the synthesis procedures of Complex I-1, Complex I-10 was prepared by replacing 8-hydroxyquinoline with 4-hydroxy-1,5-naphthyridine and $GaCl_3$ with $AlCl_3$.

After drying, the [(4-hydroxy-1,5-naphthyridine)(salicylidene-o-hydroxyanilino)aluminum] was collected and weighed 2.87 g in a yield of 75%. MS:m/e; 766, Element analysis found: C, 65.89; H, 3.56; N, 11.09; Calc.: C, 65.80; H, 3.66; N, 10.97.

Example 9

Synthesis of bis[(5-hydroxyquinoxaline)(salicylidene-o-hydroxyanilino)gallium] (Complex I-12)

According to the synthesis procedures of Complex I-1, Complex I-12 was prepared by replacing 8-hydroxyquinoline with 5-hydroxyquinoxaline.

After drying, the bis[(5-hydroxyquinoxaline)(salicylidene-o-hydroxyanilino)gallium] was collected and weighed 3.32 g in a yield of 78%. MS:m/e, 852, Element analysis found: C, 59.10; H, 3.20; N, 9.81; Calc.: C, 59.15; H, 3.29; N, 9.86.

Example 10

Synthesis of [(5-hydroxyquinoxaline)(salicylidene-o-hydroxyanilino)aluminum] (Complex I-13)

According to the synthesis procedures of Complex I-12, Complex I-13 was prepared by replacing $GaCl_3$ with $AlCl_3$.

After drying, the [(5-hydroxyquinoxaline)(salicylidene-o-hydroxyanilino)aluminum] was collected and weighed 2.87 g in a yield of 75%. MS:m/e; 766, Element analysis found: C, 65.89; H, 3.56; N, 11.09; Calc.: C, 65.80; H, 3.66; N, 10.97.

Example 11

Synthesis of bis[(5-hydroxyquinoxaline)(2-hydroxy-1-naphthylaldehyde-o-hydroxyanilino) gallium] (Complex I-14)

According to the synthesis procedures of Complex I-12, Complex I-14 was prepared by replacing 2-hydroxy-salicylic aldehyde with 2-hydroxy-1-naphthylaldehyde.

After drying, the bis[(5-hydroxyquinoxaline)(2-hydroxy-1-naphthylaldehyde-o-hydroxyanilino) gallium] was collected and weighed 3.71 g in a yield of 78%. MS:m/e; 952, Element analysis found: C, 63.00; H, 3.33; N, 8.75; Calc.: C, 63.03; H, 3.36; N, 8.82.

Example 12

Synthesis of bis[(2-(o-hydroxylphenyl)-benzimidazole)(salicylidene-o-hydroxyanilino)gallium] (Complex I-15)

According to the synthesis procedures of Complex I-1, Complex I-15 was prepared by replacing 8-hydroxyquinoline with 2-(o-hydroxylphenyl)-benzimidazole.

After drying, the bis[(2-(o-hydroxylphenyl)-benzimidazole) (salicylidene-o-hydroxyanilino)gallium] was collected and weighed 3.72 g in a yield of 76%. MS:m/e, 980, Element analysis found: C, 63.65; H, 3.65; N, 8.52; Calc.: C, 63.67; H, 3.67; N, 8.57.

Example 13

Synthesis of [(2-(o-hydroxylphenyl)-benzimidazole)(salicylidene-o-hydroxyanilino) aluminum] (Complex I-16)

According to the synthesis procedures of Complex I-15, Complex I-16 was prepared by replacing $GaCl_3$ with $AlCl_3$.

After drying, the [(2-(o-hydroxylphenyl)-benzimidazole)(salicylidene-o-hydroxyanilino)aluminum] was collected and weighed 1.76 g in a yield of 79%. MS:m/e, 447, Element analysis found: C, 69.75; H, 3.90; N, 9.25; Calc.: C, 69.80; H, 4.03; N, 9.40.

Example 14

Synthesis of bis[(2-(o-hydroxylphenyl)-benzothiazole)(salicylidene-o-hydroxyanilino)gallium] (Complex I-19)

According to the synthesis procedures of Complex I-1, Complex I-19 was prepared by replacing 8-hydroxyquinoline with 2-(o-hydroxylphenyl)-benzothiazole.

After drying, the bis[(2-(o-hydroxylphenyl)-benzothiazole)(salicylidene-o-hydroxyanilino)gallium] was collected and weighed 3.80 g in a yield of 75%. MS:m/e, 1014, Element analysis found: C, 61.50; H, 3.36; N, 5.50; Calc.: C, 61.54; H, 3.35; N, 5.52.

Example 15

Synthesis of bis[(2-(o-hydroxylphenyl)-benzothiazole)(salicylidene-o-hydroxyanilino)aluminum] (Complex I-20)

According to the synthesis procedures of Complex I-19, Complex I-20 was prepared by replacing $GaCl_3$ with $AlCl_3$.

After drying, the bis[(2-(o-hydroxylphenyl)-benzothiazole) (salicylidene-o-hydroxyanilino) aluminum] was collected and weighed 3.38 g in a yield of 74%. MS:m/e, 928, Element analysis found: C, 67.35; H, 3.49; N, 5.88; Calc.: C, 67.24; H, 3.66; N, 6.03.

Example 16

Synthesis of [(10-hydroxyl-benzoquinoline)(salicylidene-o-hydroxyanilino)gallium] (Complex I-21)

According to the synthesis procedures of Complex I-1, Complex I-21 was prepared by replacing 8-hydroxyquinoline with 10-hydroxyl-benzoquinoline.

After drying, the [(10-hydroxyl-benzoquinoline)(salicylidene-o-hydroxyanilino)gallium] was collected and weighed 1.85 g in a yield of 78%. MS:m/e, 475, Element analysis found: C, 65.67; H, 3.55; N, 5.87; Calc.: C, 65.68; H, 3.58; N, 5.89.

Example 17

Synthesis of bis[(2-carboxyl-pyridine)(salicylidene-o-hydroxyanilino)gallium] (Complex I-22)

According to the synthesis procedures of Complex I-1, Complex I-22 was prepared by replacing 8-hydroxyquinoline with 2-carboxyl-pyridine.

After drying, the bis[(2-carboxyl-pyridine)(salicylidene-o-hydroxyanilino)gallium] was collected and weighed 3.02 g in a yield of 75%. MS:m/e, 806, Element analysis found: C, 56.69; H, 3.16; N, 6.79; Calc.: C, 56.58; H, 3.23; N, 6.95.

Example 18

Synthesis of bis[(8-hydroxyquinolino)(2,2'-diol-stilbene)gallium] (Complex II-1)

Complex II-1 was synthesized through a reaction in the ethanol solution of 8-hydroxyquinoline, 2,2'-diol-stilbene ($L^3$) and $GaCl_3$. First, a solution of 8-hydroxyquinoline (0.05M) and piperidine (0.05M) in 100 ml ethanol was added to a solution of $GaCl_3$ (0.5M) in 10 ml ethanol very slowly with an intensive stirring. Then, a solution of $L^3$ (0.01M) and piperidine (0.02M) in 500 ml ethanol was introduced slowly. The mixture was stirred for about 1 hour and cooled to room temperature and kept in dark for about 1 hour. A scarlet precipitate was formed when equivalent amount water was poured into the solution. The product was collected by filtration and washed with ethanol rapidly, then dried under an infrared lamp. The obtained product powder showed strong red fluorescence under an ultraviolet lamp. The materials were further purified by an improved train sublimation method. The $L^3$ ligand was obtained by typical synthesis method of stilbene. The molecular structure of Complex II-I was supported by mass spectrum (MS) and element analysis.

After drying, the bis[(8-hydroxyquinolino)(2,2'-diol-stilbene)gallium] was collected and weighed 3.30 g in a yield of 78%. MS found: m/e, 848; Element analysis found: C, 65.16; H, 3.85; N, 3.25; Calc.: C, 65.14; H, 3.80; N, 3.30.

Example 19

Synthesis of bis[(4-methyl-8-hydroxyquinolino)(2,2'-diol-stilbene)gallium] (Complex II-4)

According to the synthesis procedures of Complex II-1, Complex I-4 was prepared by replacing 8-hydroxyquinoline with 4-methyl-8-hydroxyquinolino.

After drying, the bis[(4-methyl-8-hydroxyquinolino)(2,2'-diol-stilbene)gallium] was collected and weighed 3.37 g in a yield of 77%. MS found: m/e, 876. Element analysis found: C, 65.81; H, 4.16; N, 3.15; Calc.: C, 65.79; H, 4.14; N, 3.20.

Example 20

Synthesis of bis[(5-fluoro-8-hydroxyquinolino)(2,2'-diol-stilbene)gallium] (Complex II-6)

According to the synthesis procedures of Complex II-1, Complex II-6 was prepared by replacing 8-hydroxyquinoline with 5-fluoro-8-hydroxyquinolino.

After drying, the bis[(5-fluoro-8-hydroxyquinolino)(2,2'-diol-stilbene)gallium] was collected and weighed 3.31 g in a yield of 75%. MS found: m/e, 884. Element analysis found: C, 62.53; H, 3.46; N, 3.14; Calc.: C, 62.49; H, 3.42; N, 3.17.

Example 21

Synthesis of bis[(2-(o-hydroxyphenyl)-benzoxazole)(2,2'-diol-stilbene)gallium] (Complex II-8)

According to the synthesis procedures of Complex II-1, Complex II-8 was prepared by replacing 8-hydroxyquinoline with 2-(o-hydroxphenyl)-benzoxazole.

After drying, the bis[(2-(o-hydroxphenyl)-benzoxazole)(2,2'-diol-stilbene)gallium] was collected and weighed 3.72 g in a yield of 76%. MS found: m/e, 980. Element analysis found: C, 66.24; H, 3.58; N, 2.87; Calc.: C, 66.16; H, 3.70; N, 2.85.

Example 22

Synthesis of bis[(4-hydroxy-1,5-naphthyridine)(2,2'-diol-stilbene)gallium] (Complex II-10)

According to the synthesis procedures of Complex II-1, Complex II-10 was prepared by replacing 8-hydroxyquinoline with 4-hydroxy-1,5-naphthyridine.

After drying, the bis[(4-hydroxy-1,5-naphthyridine)(2,2'-diol-stilbene)gallium] was collected and weighed 3.23 g in a yield of 76%. MS found: m/e, 850. Element analysis found: C, 62.28; H, 3.41; N, 6.64; Calc.: C, 62.16; H, 3.55; N, 6.58.

Example 23

Synthesis of bis[(5-hydroxyquinoxaline)(2,2'-diol-stilbene) indium] (Complex II-11)

According to the synthesis procedures of Complex II-1, Complex II-11 was prepared by replacing 8-hydroxyquinoline with 5-hydroxyquinoxaline and $GaCl_3$ with $InCl_3$.

After drying, the bis[(5-hydroxyquinoxaline)(2,2'-diol-stilbene)indium] was collected and weighed 3.31 g in a yield of 78%. MS found: m/e, 940. Element analysis found: C, 59.11; H, 3.23; N, 6.31; Calc.: C, 59.04; H, 3.31; N, 6.27.

Example 24

Synthesis of bis[(2-(o-hydroxylphenyl)-benzimidazole)(2,2'-diol-stilbene)gallium] (Complex II-13)

According to the synthesis procedures of Complex II-1, Complex II-13 was prepared by replacing 8-hydroxyquinoline with 2-(o-hydroxylphenyl)-benzimidazole.

After drying, the bis[(2-(o-hydroxylphenyl)-benzimidazole)(2,2'-diol-stilbene)gallium] was collected and weighed 3.81 g in a yield of 78%. MS found: m/e, 978. Element analysis found: C, 66.26; H, 3.86; N, 5.85; Calc.: C, 66.29; H, 3.91; N, 5.73.

Example 25

Synthesis of bis[(2-(o-hydroxylphenyl)-N-phenyl-benzimidazole)(2,2'-diol-stilbene)gallium] (Complex II-15)

According to the synthesis procedures of Complex II-1, Complex II-15 was prepared by replacing 8-hydroxyquinoline with 2-(o-hydroxylphenyl)-N-phenyl-benzimidazole.

After drying, the bis[(2-(o-hydroxylphenyl)-N-phenyl-benzimidazole)(2,2'-diol-stilbene)gallium] was collected and weighed 4.29 g in a yield of 76%. MS found: m/e, 1131. Element analysis found: C, 70.10; H, 3.85; N, 4.89; Calc.: C, 70.12; H, 4.10; N, 4.96.

Example 26

Synthesis of bis[(2-(o-hydroxylphenyl)-benzothiazole)(2,2'-diol-stilbene)gallium] (Complex II-16)

According to the synthesis procedures of Complex II-1, Complex II-16 was prepared by replacing 8-hydroxyquinoline with 2-(o-hydroxylphenyl)-benzothiazole.

After drying, the bis[(2-(o-hydroxylphenyl)-benzothiazole)(2,2'-diol-stilbene)gallium] was collected and weighed 3.78 g in a yield of 74%. MS found: m/e, 1023. Element analysis found: C, 64.10; H, 3.49; N, 2.85; Calc.: C, 64.06; H, 3.58; N, 2.77.

Example 27

Synthesis of (10-hydroxyl-benzoquinoline)(2,2'-diol-stilbene)gallium (Complex II-17)

According to the synthesis procedures of Complex II-1, Complex II-17 was prepared by replacing 8-hydroxyquinoline with 10-hydroxyl-benzoquinoline.

After drying, the (10-hydroxyl-benzoquinoline)(2,2'-diol-stilbene)gallium was collected and weighed 1.89 g in a yield of 80%. MS found: m/e, 474. Element analysis found: C, 68.45; H, 3.78; N, 2.89; Calc.: C, 68.39; H, 3.83; N, 2.95.

Example 28

Synthesis of bis[(2-carboxyl-pyridine)(2,2'-diol-stilbene)gallium] (Complex II-18)

According to the synthesis procedures of Complex II-1, Complex II-18 was prepared by replacing 8-hydroxyquinoline with 2-carboxyl-pyridine.

After drying, the bis[(2-carboxyl-pyridine)(2,2'-diol-stilbene)gallium] was collected and weighed 3.05 g in a yield of 76%. MS found: m/e, 804. Element analysis found: C, 59.72; H, 3.46; N, 3.51; Calc.: C, 59.75; H, 3.51; N, 3.48.

Example 29

Synthesis of bis[(8-hydroxyquinoline)(o,o'-dihydroxyazobenzene)gallium] (Complex III-1, where n=2, M=Ga)

According to the synthesis procedures of Complex II-1, Complex III-1 was prepared by replacing salicylidene-o-aminophenol with o,o'-dihydroxyazobenzene.

After drying, the bis[(8-hydroxyquinoline)(o,o'-dihydroxyazobenzene)gallium] was collected and weighed 3.19 g in a yield of 75%. MS found: m/e, 852. Element analysis found: C, 59.10; H, 3.36; N, 9.91; Calc.: C, 59.20; H, 3.31; N, 9.86.

Example 30

Synthesis of bis[(4-methyl-8-hydroxyquinoline)(o,o'-dihydroxyazobenzene)aluminum] (Complex III-3)

According to the synthesis procedures of Complex III-1, Complex III-3 was prepared by replacing 8-hydroxyquinoline with 4-methyl-8-hydroxyquinoline and replacing $GaCl_3$ with $AlCl_3$.

After drying, the bis[(4-methyl-8-hydroxyquinoline)(o,o'-dihydroxyazobenzene)aluminum] was collected and weighed 3.43 g in a yield of 78%. MS found: m/e, 795. Element analysis found: C, 62.84; H, 3.63; N, 10.15; Calc.: C, 63.12; H, 3.73; N, 10.01.

Example 31

Synthesis of bis[(5-fluoro-8-hydroxyquinoline)(o,o'-dihydroxyazobenzene)gallium] (Complex III-5, where n=2, M=Ga)

According to the synthesis procedures of Complex III-1, Complex III-5 was prepared by replacing 8-hydroxyquinoline with 5-fluoro-8-hydroxyquinoline.

After drying, the bis[(5-fluoro-8-hydroxyquinoline)(o,o'-dihydroxyazobenzene)gallium] was collected and weighed 3.42 g in a yield of 77%. MS found: m/e, 888. Element analysis found: C, 56.96; H, 2.85; N, 9.47; Calc.: C, 56.80; H, 2.95; N, 9.46.

Example 32

Synthesis of bis[(2-(o-hydroxyphenyl)-benzoxazole)(o,o'-dihydroxyazobenzene)gallium] (Complex III-6)

According to the synthesis procedures of Complex III-1, Complex III-6 was prepared by replacing 8-hydroxyquinoline with 2-(o-hydroxyphenyl)-benzoxazole.

After drying, the bis[(2-(o-hydroxyphenyl)-benzoxazole)(o,o'-dihydroxyazobenzene)gallium] was collected and weighed 3.64 g in a yield of 74%. MS found: m/e, 984. Element analysis found: C, 60.89; H, 3.25; N, 8.65; Calc.: C, 61.01; H, 3.28; N, 8.54.

Example 33

Synthesis of bis[(4-hydroxy-1,5-naphthyridine)(o,o'-dihydroxyazobenzene)gallium] (Complex III-9)

According to the synthesis procedures of Complex III-1, Complex III-9 was prepared by replacing 8-hydroxyquinoline with 4-hydroxy-1,5-naphthyridine.

After drying, the bis[(4-hydroxy-1,5-naphthyridine)(o,o'-dihydroxyazobenzene)gallium] was collected and weighed 3.24 g in a yield of 76%. MS found: m/e, 854. Element analysis found: C, 56.26; H, 2.98; N, 13.25; Calc.: C, 56.25; H, 3.07; N, 13.12.

Example 34

Synthesis of bis[(5-hydroxyquinoxaline)(o,o'-dihydroxyazobenzene)gallium] (Complex III-10)

According to the synthesis procedures of Complex III-1, Complex III-10 was prepared by replacing 8-hydroxyquinoline with 5-hydroxyquinoxaline.

After drying, the bis[(5-hydroxyquinoxaline)(o,o'-dihydroxyazobenzene)gallium] was collected and weighed 3.28 g in a yield of 77%. MS found: m/e, 854. Element analysis found: C, 56.26; H, 2.98; N, 13.25; Calc.: C, 56.25; H, 3.07; N, 13.12.

Example 35

Synthesis of bis[(2-(o-hydroxylphenyl)-benzimidazole)(o,o'-dihydroxyazobenzene)gallium] (Complex III-12)

According to the synthesis procedures of Complex III-1, Complex III-12 was prepared by replacing 8-hydroxyquinoline with 2-(o-hydroxylphenyl)-benzimidazole.

After drying, the bis[(2-(o-hydroxylphenyl)-benzimidazole)(o,o'-dihydroxyazobenzene)gallium] was collected and weighed 3.82 g in a yield of 78%. MS found: m/e, 982. Element analysis found: C, 60.89; H, 3.56; N, 11.45; Calc.: C, 61.14; H, 3.49; N, 11.41.

Example 36

Synthesis of bis[(2-(o-hydroxylphenyl)-N-phenyl-benzimidazole)(o,o'-dihydroxyazobenzene) gallium] (Complex III-14)

According to the synthesis procedures of Complex III-1, Complex III-14 was prepared by replacing 8-hydroxyquinoline with 2-(o-hydroxylphenyl)-N-phenyl-benzimidazole.

After drying, the bis[(2-(o-hydroxylphenyl)-N-phenyl-benzimidazole)(o,o'-dihydroxyazobenzene)gallium] was collected and weighed 4.37 g in a yield of 77%. MS found: m/e, 1135. Element analysis found: C, 65.71; H, 3.64; N, 9.95; Calc.: C, 65.64, H, 3.73; N, 9.88.

Example 37

Synthesis of bis[(2-(o-hydroxylphenyl)-benzothiazole)(o,o'-dihydroxyazobenzene)gallium] (Complex III-15)

According to the synthesis procedures of Complex III-1, Complex III-15 was prepared by replacing 8-hydroxyquinoline with 2-(o-hydroxylphenyl)-benzothiazole.

After drying, the bis[(2-(o-hydroxylphenyl)-benzothiazole)(o,o'-dihydroxyazobenzene)gallium] was collected and weighed 3.86 g in a yield of 76%. MS found: m/e, 1016. Element analysis found: C, 58.89; H, 3.26; N, 8.33; Calc.: C, 59.08; H, 3.17; N, 8.29.

Example 38

Synthesis of (10-hydroxyl-benzoquinoline)(o,o'-dihydroxyazobenzene)gallium (Complex III-16)

According to the synthesis procedures of Complex III-1, Complex III-16 was prepared by replacing 8-hydroxyquinoline with 10-hydroxyl-benzoquinoline.

After drying, the (10-hydroxyl-benzoquinoline)(o,o'-dihydroxyazobenzene)gallium was collected and weighed 1.88 g in a yield of 79%. MS found: m/e, 476. Element analysis found: C, 62.89; H, 3.45; N, 8.79; Calc.: C, 63.06; H, 3.39; N, 8.83.

Example 39

Synthesis of bis[(2-carboxyl-pyridine)(o,o'-dihydroxyazobenzene)gallium] (Complex III-17)

According to the synthesis procedures of Complex III-1, Complex III-17 was prepared by replacing 8-hydroxyquinoline with 2-carboxyl-pyridine.

After drying, the bis[(2-carboxyl-pyridine)(o,o'-dihydroxyazobenzene)gallium] was collected and weighed 2.99 g in a yield of 74%. MS found: m/e, 808. Element analysis found: C, 53.45; H, 2.84; N, 10.62; Calc.: C, 53.51; H, 2.99; N, 10.40.

Example 40

Synthesis of bis[(acetylacetone)(salicylidene-o-hydroxyanilino)aluminum] ([Al(saph)acac]$_2$, Complex IV-1)

According to the synthesis procedures of Complex I-1, Complex IV-1 was prepared by replacing 8-hydroxyquinoline with acetylacetone and replacing GaCl$_3$ with AlCl$_3$, respectively.

After drying, the bis[(acetylacetone)(salicylidene-o-hydroxyanilino)aluminum] was collected and weighed 2.43 g in a yield of 72%. MS found: m/e, 676. Element analysis found: C, 64.05; H, 5.12; N, 4.15; Calc.: C, 63.90; H, 5.06; N, 4.14.

Example 41

Synthesis of bis[(acetylacetone)(salicylidene-o-hydroxyanilino)gallium] ([Ga(saph)acac]$_2$, Complex IV-2)

According to the synthesis procedures of Complex IV-1, Complex IV-2 was prepared by replacing AlCl$_3$ with GaCl$_3$.

After drying, the bis[(acetylacetone)(salicylidene-o-hydroxyanilino)gallium] was collected and weighed 2.74 g in a yield of 72%. MS found: m/e, 762. Element analysis found: C, 56.73; H, 4.496; N, 3.67; Calc.: C, 56.12; H, 4.166; N, 3.28.

Example 42

Synthesis of bis[(acetylacetone)(salicylidene-2-hydroxyl-1-naphthylamine)gallium] (Complex IV-3)

According to the synthesis procedures of Complex IV-2, Complex IV-3 was prepared by replacing salicylidene-o-hydroxyaniline with salicylidene-2-hydroxyl-1-naphthylamine.

After drying, the bis[(acetylacetone)(salicylidene-2-hydroxyl-1-naphthylamine)gallium] was collected and weighed 2.78 g in a yield of 73%. MS found: m/e, 762. Element analysis found: C, 56.82; H, 4.34; N, 3.72; Calc.: C, 56.73; H, 4.49; N, 3.67.

Example 43

Synthesis of bis[(2,2-dimethyl-3,5-hexanedione)(salicylidene-o-hydroxyanilino)aluminum] (Complex IV-5)

According to the synthesis procedures of Complex IV-1, Complex IV-5 was prepared by replacing acetylacetone with 2,2-dimethyl-3,5-hexanedione.

After drying, the bis[(2,2-dimethyl-3,5-hexanedione)(salicylidene-o-hydroxyanilino)aluminum] was collected and weighed 2.89 g in a yield of 76%. MS found: m/e, 760. Element analysis found: C, 66.41; H, 5.89; N, 3.67; Calc.: C, 66.30; H, 6.09; N, 3.68.

Example 44

Synthesis of bis[(2-methyl-3,5-hexanedione)(salicylidene-o-hydroxyanilino)aluminum] (Complex IV-6)

According to the synthesis procedures of Complex IV-1, Complex IV-6 was prepared by replacing acetylacetone with 2-methyl-3,5-hexanedione.

After drying, the bis[(2-methyl-3,5-hexanedione)(salicylidene-o-hydroxyanilino)aluminum] was collected and weighed 2.74 g in a yield of 75%. MS found: m/e, 732. Element analysis found: C, 65.64; H, 5.62; N, 3.91; Calc.: C, 65.56; H, 5.77; N, 3.82.

Example 45

Synthesis of bis[(2,2,6,6-tetramethyl-3,5-heptanedione)(salicylidene-o-hydroxyanilino) aluminum] (Complex IV-8)

According to the synthesis procedures of Complex IV-1, Complex IV-8 was prepared by replacing acetylacetone with 2,2,6,6-tetramethyl-3,5-heptanedione.

After drying, the bis[(2,2,6,6-tetramethyl-3,5-heptanedione) (salicylidene-o-hydroxyanilino) aluminum] was collected and weighed 3.12 g in a yield of 74%. MS found: m/e, 844. Element analysis found: C, 68.34; H, 6.85; N, 3.27; Calc.: C, 68.23; H, 6.91; N, 3.31.

Example 46

Synthesis of bis[(1,1,1-trifluoro-5,5-dimethyl-2,4-hexanedione)(salicylidene-o-hydroxyanilino) gallium] (Complex IV-9)

According to the synthesis procedures of Complex IV-1, Complex IV-9 was prepared by replacing acetylacetone with 1,1,1-trifluoro-5,5-dimethyl-2,4-hexanedione and AlCl$_3$ with GaCl$_3$.

After drying, the bis[(1,1,1-trifluoro-5,5-dimethyl-2,4-hexanedione)(salicylidene-o-hydroxyanilino)gallium] was collected and weighed 3.38 g in a yield of 78%. MS found: m/e, 953. Element analysis found: C, 52.89; H, 4.15; N, 2.85; Calc.: C, 52.73; H, 4.27; N, 2.91.

Example 47

Synthesis of bis[(1,1,1-trifluoro-4-phenyl-2,4-butadione)(salicylidene-o-hydroxyanilino) aluminum] (Complex IV-11)

According to the synthesis procedures of Complex IV-1, Complex IV-11 was prepared by replacing acetylacetone with 1,1,1-trifluoro-4-phenyl-2,4-butadione.

After drying, the bis[(1,1,1-trifluoro-4-phenyl-2,4-butadione)(salicylidene-o-hydroxyanilino) aluminum] was collected and weighed 3.32 g in a yield of 72%. MS found: m/e, 924. Element analysis found: C, 72.85; H, 4.46; N, 2.89; Calc.: C, 72.72; H, 4.57; N, 3.02.

Example 48

Synthesis of bis[(dibenzoylmethene)(salicylidene-o-hydroxyanilino)aluminum] (Complex IV-12)

According to the synthesis procedures of Complex IV-1, Complex IV-12 was prepared by replacing acetylacetone with dibenzoylmethene.

After drying, the bis[(dibenzoylmethene)(salicylidene-o-hydroxyanilino)aluminum] was collected and weighed 3.51 g in a yield of 76%. MS found: m/e, 924. Element analysis found: C, 72.72; H, 4.57; N, 3.02; Calc.: C, 71.95; H, 4.21; N, 2.93.

Example 49

Synthesis of bis[(thenoyltrifluoroacetone)(salicylidene-o-hydroxyanilino)aluminum] (Complex IV-14)

According to the synthesis procedures of Complex IV-1, Complex IV-14 was prepared by replacing acetylacetone with thenoyltrifluoroacetone.

After drying, the bis[(thenoyltrifluoroacetone)(salicylidene-o-hydroxyanilino)aluminum] was collected and weighed 3.22 g in a yield of 70%. MS found: m/e, 920. Element analysis found: C, 54.85; H, 2.87; N, 3.12; Calc.: C, 54.78; H, 3.06; N, 3.04.

Example 50

Synthesis of bis[(4,4,4-trifluoro-1-(2-furyl)-1,3-butanedione)(salicylidene-o-hydroxyanilino) gallium] (Complex IV-16)

According to the synthesis procedures of Complex IV-1, Complex IV-16 was prepared by replacing acetylacetone with 4,4,4-trifluoro-1-(2-furyl)-1,3-butanedione and replacing $AlCl_3$ with $GaCl_3$ respectively.

After drying, the bis[(4,4,4-trifluoro-1-(2-furyl)-1,3-butanedione)(salicylidene-o-hydroxyanilino)gallium] was collected and weighed 3.33 g in a yield of 75%. MS found: m/e, 973. Element analysis found: C, 51.72; H, 2.81; N, 2.91; Calc.: C, 51.56; H, 2.95; N, 2.86.

Example 51

Synthesis of (3-(9-anthryl) pentane-2,4-dione)(salicylidene-o-hydroxyanilino)aluminum (Complex IV-21)

According to the synthesis procedures of Complex IV-1, Complex IV-21 was prepared by replacing acetylacetone with 3-(9-anthryl) pentane-2,4-dione).

After drying, the (3-(9-anthryl)pentane-2,4-dione)(salicylidene-o-hydroxyanilino)aluminum was collected and weighed 1.93 g in a yield of 73%. MS found: m/e, 528. Element analysis found: C, 75.05; H, 5.06; N, 2.59; Calc.: C, 74.98; H 5.14; N, 2.64.

Example 52

Synthesis of (1-phenyl-3-methyl-4-acetylpyrazol-5-one)(salicylidene-o-hydroxyanilino)aluminum (Complex IV-22)

According to the synthesis procedures of Complex IV-1, Complex IV-22 was prepared by replacing acetylacetone with 1-phenyl-3-methyl-4-acetylpyrazol-5-one.

After drying, the (1-phenyl-3-methyl-4-acetylpyrazol-5-one)(salicylidene-o-hydroxyanilino) aluminum was collected and weighed 1.68 g in a yield of 74%. MS found: m/e, 454. Element analysis found: C, 66.12; H, 4.58; N, 9.36; Calc.: C, 66.07; H, 4.65; N, 9.24.

Example 53

Synthesis of (1-phenyl-3-methyl-4-phenylacetylpyrazol-5-one)(salicylidene-o-hydroxyanilino) aluminum (Complex IV-23)

According to the synthesis procedures of Complex IV-1, Complex IV-23 was prepared by replacing acetylacetone with 1-phenyl-3-methyl-4-phenylacetylpyrazol-5-one.

After drying, the (1-phenyl-3-methyl-4-phenylacetylpyrazol-5-one)(salicylidene-o-hydroxyanilino)aluminum was collected and weighed 2.01 g in a yield of 78%. MS found: m/e, 516. Element analysis found: C, 69.85; H, 4.36; N, 8.13; Calc.: C, 69.76; H, 4.48; N, 8.13.

Example 54

Synthesis of (1-phenyl-3-methyl-4-trifluoro-methylacetylpyrazol-5-one)(salicylidene-o-hydroxyanilino) aluminum (Complex IV-24)

According to the synthesis procedures of Complex IV-1, Complex IV-24 was prepared by replacing acetylacetone with 1-phenyl-3-methyl-4-trifluoro-methylacetylpyrazol-5-one.

After drying, the (1-phenyl-3-methyl-4-trifluoro-methylacetylpyrazol-5-one)(salicylidene-o-hydroxyanilino)aluminum was collected and weighed 1.91 g in a yield of 75%. MS found: m/e, 509. Element analysis found: C, 59.02; H, 3.68; N, 8.27; Calc.: C, 58.94; H, 3.75; N, 8.24.

Example 55

Synthesis of bis[(2-hydroxy-5-(trifluoromethoxy)benzaldehyde)(salicylidene-o-hydroxyanilino) aluminum] (Complex IV-26)

According to the synthesis procedures of Complex IV-1, Complex IV-26 was prepared by replacing acetylacetone with 1-phenyl-3-methyl-4-phenylacetylpyrazol-5-one.

After drying bis[(2-hydroxy-5-(trifluoromethoxy)benzaldehyde)(salicylidene-o-hydroxyanilino) aluminum] was collected and weighed 2.83 g in a yield of 76%. MS found: m/e, 746. Element analysis found: C, 67.69; H, 4.25; N, 3.76; Calc.: C, 67.56; H, 4.31; N, 3.75.

Example 56

Synthesis of bis[(acetylacetone)(2,2'-diol-stilbene)aluminum] (Complex V-1)

According to the synthesis procedures of Complex I-1, Complex V-1 was prepared by replacing 8-hydroxyquinoline with acetylacetone, replacing $GaCl_3$ with $AlCl_3$, and replacing salicylidene-o-hydroxyaniline with 2,2'-diol-stilbene, respectively.

After drying, the bis[(acetylacetone)(2,2'-diol-stilbene)aluminum] was collected and weighed 2.78 g in a yield of 72%. MS found: m/e, 774. Element analysis found: C, 67.80; H, 5.26; Calc.: C, 67.65; H, 5.37.

Example 57

Synthesis of bis[(2,2-dimethyl-3,5-hexanedione)(2,2'-diol-stilbene)aluminum] (Complex V-4)

According to the synthesis procedures of Complex V-1, Complex V-4 was prepared by replacing acetylacetone with 2,2-dimethyl-3,5-hexanedione.

After drying, the bis[(2,2-dimethyl-3,5-hexanedione)(2,2'-diol-stilbene)aluminum] was collected and weighed 2.69 g in a yield of 71%. MS found: m/e, 758. Element analysis found: C, 69.85; H, 6.26; Calc.: C, 69.64; H, 6.37.

Example 58

Synthesis of bis[(2-methyl-3,5-hexanedione)(2,2'-diol-stilbene)aluminum] (Complex V-5)

According to the synthesis procedures of Complex V-1, Complex V-5 was prepared by replacing acetylacetone with 2-methyl-3,5-hexanedione.

After drying, the bis[(2-methyl-3,5-hexanedione)(2,2'-diol-stilbene)aluminum] was collected and weighed 2.73 g in a yield of 75%. MS found: m/e, 730. Element analysis found: C, 68.89; H, 6.10; Calc.: C, 69.03; H, 6.06.

Example 59

Synthesis of bis[(2,2,6,6-tetramethyl-3,5-heptanedione)(2,2'-diol-stilbene)aluminum] (Complex V-7)

According to the synthesis procedures of Complex V-1, Complex V-7 was prepared by replacing acetylacetone with 2,2,6,6-tetramethyl-3,5-heptanedione.

After drying, the bis[(2,2,6,6-tetramethyl-3,5-heptanedione)(2,2'-diol-stilbene)aluminum] was collected and weighed 3.03 g in a yield of 72%. MS found: m/e, 842. Element analysis found: C, 71.36; H, 1.15; Calc.: C, 71.24; H, 7.17.

Example 60

Synthesis of bis[(1,1,1-trifluoro-5,5-dimethyl-2,4-hexanedione)(2,2'-diol-stilbene)aluminum] (Complex V-8)

According to the synthesis procedures of Complex V-1, Complex V-8 was prepared by replacing acetylacetone with 1,1,1-trifluoro-5,5-dimethyl-2,4-hexanedione.

After drying, the bis[(1,1,1-trifluoro-5,5-dimethyl-2,4-hexanedione)(2,2'-diol-stilbene)aluminum] was collected and weighed 3.20 g in a yield of 74%. MS found: m/e, 866. Element analysis found: C, 61.16; H, 4.69; Calc.: C, 60.97; H, 4.88.

Example 61

Synthesis of bis[(1,1,1-trifluoro-4-phenyl-2,4-butadione)(2,2'-diol-stilbene)gallium] (Complex V-10)

According to the synthesis procedures of Complex V-1, Complex V-10 was prepared by replacing acetylacetone with 1,1,1-trifluoro-4-phenyl-2,4-butadione and $AlCl_3$ with $GaCl_3$.

After drying, the bis[(1,1,1-trifluoro-4-phenyl-2,4-butadione)(2,2'-diol-stilbene)gallium] was collected and weighed 3.44 g in a yield of 76%. MS found: m/e, 991. Element analysis found: C, 57.93; H, 3.28; Calc.: C, 57.85; H, 3.32.

Example 62

Synthesis of bis[(dibenzoylmethene)(2,2'-diol-stilbene)aluminum] (Complex V-11)

According to the synthesis procedures of Complex V-1, Complex V-11 was prepared by replacing acetylacetone with dibenzoylmethene.

After drying, the bis[(dibenzoylmethene)(2,2'-diol-stilbene)aluminum] was collected and weighed 3.45 g in a yield of 75%. MS found: m/e, 922. Element analysis found: C, 75.56; H, 4.69; Calc.: C, 75.48; H, 4.80.

Example 63

Synthesis of bis[(thenoyltrifluoroacetone)(2,2'-diol-stilbene)aluminum] (Complex V-14)

According to the synthesis procedures of Complex V-1, Complex V-14 was prepared by replacing acetylacetone with thenoyltrifluoroacetone.

After drying, the bis[(thenoyltrifluoroacetone)(2,2'-diol-stilbene)aluminum] was collected and weighed 3.93 g in a yield of 71%. MS found: m/e, 1108. Element analysis found: C, 75.83; H, 5.19; N, 2.46; Calc.: C, 75.79; H, 5.27; N, 2.52.

Example 64

Synthesis of bis[(4,4,4-trifluoro-1-(2-furyl)-1,3-butanedione)(2,2'-diol-stilbene)aluminum] (Complex V-15)

According to the synthesis procedures of Complex V-1, Complex V-15 was prepared by replacing acetylacetone with 4,4,4-trifluoro-1-(2-furyl)-1,3-butanedione.

After drying, the bis[(4,4,4-trifluoro-1-(2-furyl)-1,3-butanedione)(2,2'-diol-stilbene)aluminum] was collected and weighed 3.18 g in a yield of 72%. MS found: m/e, 886. Element analysis found: C, 59.72; H, 3.32; Calc.: C, 59.60; H, 3.41.

Example 65

Synthesis of (3-(9-anthryl) pentane-2,4-dione)(2,2'-diol-stilbene)aluminum (Complex V-19)

According to the synthesis procedures of Complex V-1, Complex V-19 was prepared by replacing acetylacetone with 3-(9-anthryl) pentane-2,4-dione).

After drying, the (3-(9-anthryl) pentane-2,4-dione)(2,2'-diol-stilbene)aluminum was collected and weighed 1.97 g in a yield of 75%. MS found: m/e, 527. Element analysis found: C, 77.52; H, 5.26; Calc.: C, 77.40; H, 5.34.

Example 66

Synthesis of (1-phenyl-3-methyl-4-acetylpyrazol-5-one)(2,2'-diol-stilbene)aluminum (Complex V-21)

According to the synthesis procedures of Complex V-1, Complex V-21 was prepared by replacing acetylacetone with 1-phenyl-3-methyl-4-acetylpyrazol-5-one.

After drying, the (1-phenyl-3-methyl-4-acetylpyrazol-5-one)(2,2'-diol-stilbene)aluminum was collected and weighed 1.63 g in a yield of 72%. MS found: m/e, 453. Element analysis found: C, 68.87; H, 4.72; N, 6.23; Calc.: C, 68.86; H 4.88; N, 6.17.

Example 67

Synthesis of (1-phenyl-3-methyl-4-phenylacetylpyrazol-5-one)(2,2'-diol-stilbene)aluminum (Complex V-22)

According to the synthesis procedures of Complex V-1, Complex V-22 was prepared by replacing acetylacetone with 1-phenyl-3-methyl-4-phenylacetylpyrazol-5-one.

After drying, the (1-phenyl-3-methyl-4-phenylacetylpyrazol-5-one)(2,2'-diol-stilbene)aluminum was collected and weighed 1.95 g in a yield of 76%. MS found: m/e, 515. Element analysis found: C, 72.38; H, 4.51; N, 5.46; Calc.: C, 72.22; H, 4.69; N, 5.43.

Example 68

Synthesis of (1-phenyl-3-methyl-4-trifluoro-methylacetylpyrazol-5-one)(2,2'-diol-stilbene) aluminum (Complex V-23)

According to the synthesis procedures of Complex V-1, Complex V-23 was prepared by replacing acetylacetone with 1-phenyl-3-methyl-4-trifluoro-methylacetylpyrazol-5-one.

After drying, the (1-phenyl-3-methyl-4-trifluoro-methylacetylpyrazol-5-one)(2,2'-diol-stilbene) Aluminum was collected and weighed 1.83 g in a yield of 72%. MS found: m/e, 508. Element analysis found: C, 61.50; H, 3.79; N, 5.54; Calc.: C, 61.42; H, 3.96; N, 5.51.

Example 69

Synthesis of bis[(2-hydroxy-5-(trifluoromethoxy)benzaldehyde)(2,2'-diol-stilbene)aluminum] (Complex V-25)

According to the synthesis procedures of Complex V-1, Complex V-25 was prepared by replacing acetylacetone with 2-hydroxy-5-(trifluoromethoxy)benzaldehyde.

After drying, the bis[(2-hydroxy-5-(trifluoromethoxy)benzaldehyde)(2,2'-diol-stilbene)aluminum] was collected and weighed 3.21 g in a yield of 73%. MS found: m/e, 880. Element analysis found: C, 62.77; H, 3.52; Calc.: C, 62.73; H, 3.66.

Example 70

Synthesis of bis[(acetylacetone)(o,o'-dihydroxyazobenzene)aluminum] (Complex VI-1)

According to the synthesis procedures of Complex I-1, Complex VI-1 was prepared by replacing 8-hydroxyquinoline with acetylacetone, replacing $GaCl_3$ with $AlCl_3$, and replacing salicylidene-o-hydroxyaniline with o,o'-dihydroxyazobenzene, respectively.

After drying, the bis[(acetylacetone)(o,o'-dihydroxyazobenzene)aluminum] was collected and weighed 2.54 g in a yield of 75%. MS found: m/e, 678. Element analysis found: C, 60.12; H, 4.62; N, 8.29; Calc.: C, 60.17; H, 4.75; N, 8.25.

Example 71

Synthesis of bis[(2,2-dimethyl-3,5-hexanedione)(o,o'-dihydroxyazobenzene)aluminum] (Complex VI-4)

According to the synthesis procedures of Complex VI-1, Complex VI-4 was prepared by replacing acetylacetone with 2,2-dimethyl-3,5-hexanedione.

After drying, the bis[(2,2-dimethyl-3,5-hexanedione)(o,o'-dihydroxyazobenzene)aluminum] was collected and weighed 2.70 g in a yield of 71%. MS found: m/e, 762. Element analysis found: C, 63.09; H, 5.74; N, 7.38; Calc.: C, 62.98; H, 5.81; N 7.34.

Example 72

Synthesis of bis[(2-methyl-3,5-hexanedione)(o,o'-dihydroxyazobenzene)aluminum] (Complex VI-5)

According to the synthesis procedures of Complex VI-1, Complex VI-5 was prepared by replacing acetylacetone with 2-methyl-3,5-hexanedione.

After drying, the bis[(2-methyl-3,5-hexanedione)(o,o'-dihydroxyazobenzene)aluminum] was collected and weighed 2.64 g in a yield of 72%. MS found: m/e, 734. Element analysis found: C, 62.28; H, 5.35; N, 7.69; Calc.: C, 62.12; H, 5.48; N, 7.62.

Example 73

Synthesis of bis[(2,2,6,6-tetramethyl-3,5-heptanedione)(o,o'-dihydroxyazobenzene)aluminum] (Complex VI-7)

According to the synthesis procedures of Complex VI-1, Complex VI-7 was prepared by replacing acetylacetone with 2,2,6,6-tetramethyl-3,5-heptanedione.

After drying, the bis[(2,2,6,6-tetramethyl-3,5-heptanedione)(o,o'-dihydroxyazobenzene) aluminum] was collected and weighed 3.21 g in a yield of 76%. MS found: m/e, 846. Element analysis found: C, 65.38; H, 6.54; N, 6.74; Calc.: C, 65.23; H, 6.66; N, 6.61.

Example 74

Synthesis of bis[(1,1,1-trifluoro-5,5-dimethyl-2,4-hexanedione)(o,o'-dihydroxyazobenzene) gallium] (Complex VI-8)

According to the synthesis procedures of Complex VI-1, Complex VI-8 was prepared by replacing acetylacetone with 1,1,1-trifluoro-5,5-dimethyl-2,4-hexanedione and replacing $AlCl_3$ with $GaCl_3$.

After drying, the bis[(1,1,1-trifluoro-5,5-dimethyl-2,4-hexanedione)(o,o'-dihydroxy-azobenzene)gallium] was collected and weighed 3.08 g in a yield of 71%. MS found: m/e, 955. Element analysis found: C, 50.23; H, 3.91; N, 5.79; Calc.: C, 50.19; H, 4.07; N, 5.85.

Example 75

Synthesis of bis[(1,1,1-trifluoro-4-phenyl-2,4-butadione)(o,o'-dihydroxyazobenzene)aluminum] (Complex VI-10)

According to the synthesis procedures of Complex VI-1, Complex VI-10 was prepared by replacing acetylacetone with 1,1,1-trifluoro-4-phenyl-2,4-butadione.

After drying, the bis[(1,1, 1-trifluoro-4-phenyl-2,4-butadione)(o,o'-dihydroxyazobenzene) aluminum] was collected and weighed 3.32 g in a yield of 73%. MS found: m/e, 910. Element analysis found: C, 58.10; H, 3.28; N, 6.18; Calc.: C, 58.03; H, 3.32; N, 6.15.

Example 76

Synthesis of bis[(dibenzoylmethene)(o,o'-dihydroxyazobenzene)aluminum] (Complex VI-11)

According to the synthesis procedures of Complex VI-1, Complex VI-11 was prepared by replacing acetylacetone with dibenzoylmethene.

After drying, the bis[(dibenzoylmethene)(o,o'-dihydroxyazobenzene)aluminum] was collected and weighed 3.42 g in a yield of 74%. MS found: m/e, 926. Element analysis found: C, 70.02; H, 4.32; N, 6.10; Calc.: C, 69.97; H, 4.35; N, 6.04.

Example 77

Synthesis of bis[(thenoyltrifluoroacetone)(o,o'-dihydroxyazobenzene)aluminum] (Complex VI-13)

According to the synthesis procedures of Complex VI-1, Complex VI-13 was prepared by replacing acetylacetone with thenoyltrifluoroacetone.

After drying, the bis[(thenoyltrifluoroacetone)(o,o'-dihydroxyazobenzene)aluminum] was collected and weighed 3.45 g in a yield of 75%. MS found: m/e, 922. Element analysis found: C, 52.14; H, 2.76; N, 6.03; Calc.: C, 52.06; H, 2.84; N, 6.07.

Example 78

Synthesis of bis[(4,4,4-trifluoro-1-(2-furyl)-1,3-butanedione)(o,o'-dihydroxyazobenzene) aluminum] (Complex VI-14)

According to the synthesis procedures of Complex VI-1, Complex VI-14 was prepared by replacing acetylacetone with 4,4,4-trifluoro-1-(2-furyl)-1,3-butanedione.

After drying, the bis[(4,4,4-trifluoro-1-(2-furyl)-1,3-butanedione)(o,o'-dihydroxyazobenzene) aluminum] was collected and weighed 3.16 g in a yield of 71%. MS found: m/e, 890. Element analysis found: C, 53.86; H, 2.85; N, 6.24; Calc.: C, 53.94; H, 2.94; N, 6.29.

Example 79

Synthesis of (3-(9-anthryl) pentane-2,4-dione)(o,o'-dihydroxyazobenzene)aluminum (Complex VI-18)

According to the synthesis procedures of Complex VI-1, Complex VI-18 was prepared by replacing acetylacetone with 3-(9-anthryl) pentane-2,4-dione).

After drying, the (3-(9-anthryl) pentane-2,4-dione)(o,o'-dihydroxyazobenzene)aluminum was collected and weighed 1.85 g in a yield of 72%. MS found: m/e, 516. Element analysis found: C, 63.25; H, 4.68; N, 12.18; Calc.: C, 63.16; H, 4.64; N, 12.27.

Example 80

Synthesis of (1-phenyl-3-methyl-4-acetylpyrazol-5-one)(o, o'-dihydroxyazobenzene)aluminum (Complex VI-19)

According to the synthesis procedures of Complex V-1, Complex V-19 was prepared by replacing acetylacetone with 1-phenyl-3-methyl-4-acetylpyrazol-5-one.

After drying, the (1-phenyl-3-methyl-4-acetylpyrazol-5-one)(o,o'-dihydroxyazobenzene) Aluminum was collected and weighed 1.73 g in a yield of 76%. MS found: m/e, 455. Element analysis found: C, 63.15; H, 4.56; N, 12.36; Calc.: C, 63.29; H, 4.43; N, 12.30.

Example 81

Synthesis of (1-phenyl-3-methyl-4-phenylacetylpyrazol-5-one)(o,o'-dihydroxyazobenzene) gallium (Complex VI-20)

According to the synthesis procedures of Complex VI-1, Complex VI-20 was prepared by replacing acetylacetone with 1-phenyl-3-methyl-4-phenylacetylpyrazol-5-one and replacing $AlCl_3$ with $GaCl_3$.

After drying, the (1-phenyl-3-methyl-4-phenylacetylpyrazol-5-one)(o,o'-dihydroxyazobenzene) gallium was collected and weighed 1.83 g in a yield of 71%. MS found: m/e, 560. Element analysis found: C, 62.23; H, 3.93; N, 9.43; Calc.: C, 62.15; H, 4.02; N, 9.49.

Example 82

Synthesis of (1-phenyl-3-methyl-4-trifluoro-methylacetylpyrazol-5-one)(o,o'-dihydroxyazobenzene) Aluminum (Complex VI-21)

According to the synthesis procedures of Complex VI-1, Complex VI-21 was prepared by replacing acetylacetone with 1-phenyl-3-methyl-4-trifluoro-methylacetylpyrazol-5-one.

After drying, the (1-phenyl-3-methyl-4-trifluoro-methylacetylpyrazol-5-one)(o,o'-dihydroxy-azobenzene) aluminum was collected and weighed 1.93 g in a yield of 75%. MS found: m/e, 510. Element analysis found: C, 56.58; H, 3.65; N, 10.87; Calc.: C, 56.47; H, 3.55; N, 10.97.

Example 83

Synthesis of bis[(2-hydroxy-5-(trifluoromethoxy) benzaldehyde)(o,o'-dihydroxyazobenzene) aluminum] (Complex VI-23)

According to the synthesis procedures of Complex VI-1, Complex VI-23 was prepared by replacing acetylacetone with 1-phenyl-3-methyl-4-phenylacetylpyrazol-5-one.

After drying, the bis[(2-hydroxy-5-(trifluoromethoxy) benzaldehyde)(o,o'-dihydroxyazobenzene) aluminum] was collected and weighed 3.18 g in a yield of 72%. MS found: m/e, 884. Element analysis found: C, 56.89; H, 3.24; N, 6.25; Calc.: C, 57.02; H, 3.19; N, 6.33.

EL Device Fabrication by Evaporation and their Performance

Example 84

An exemplary EL device satisfying the requirements of the invention was constructed in the following manner. The organic EL medium has two organic layers; namely, a hole transport layer and an electron-transport and emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) The substrate was put in the vacuum of $1 \times 10^{-5}$–$1 \times 10^{-4}$ Pa. A hole transport layer of N,N'-bis-(1-naphthyl)-N,N'-diphenylbenzidine (400 Angstroms) was then deposited on top of the ITO coated substrate by evaporation. The deposit rate was about 0.1–0.2 nm/s.

c) The substrate was put in the vacuum of $1 \times 10^{-5}$–$1 \times 10^{-4}$ Pa. An electron-transport and emitting layer of bis[(8-hydroxyquinolino)(salicylidene-o-hydroxyanilino)gallium] ($Ga_2(saph)_2q_2$) from example 1 (400 Angstroms) was then deposited onto the hole-transport layer by evaporation. The deposit rate was about 0.1–0.2 nm/s.

d) The substrate was put in the vacuum of $1 \times 10^{-5}$–$1 \times 10^{-4}$ Pa. On top of the $Ga_2(saph)_2q_2$ layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

The light output from this EL device was 220 cd/m² when it was driven by a current source at 20 mA/cm². The maximum brightness of the device was up to 4400 cd/m² (at 25V) and the EL emission was at around 578 nm.

Example 85

An exemplary EL device satisfying the requirements of the invention was constructed in the following manner. The organic EL medium has two organic layers, namely, a hole transport layer, a doped emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) The substrate was put in the vacuum of $1 \times 10^{-5}$–$1 \times 10^{-4}$ Pa. A hole transport layer of N,N'-bis-(1-naphthyl)-N,N'-diphenylbenzidine (400 Angstroms) was then deposited on top of the ITO coated substrate by evaporation. The deposit rate was about 0.1–0.2 nm/s.

c) The substrate was put in the vacuum of $1 \times 10^{-5}$–$1 \times 10^{-4}$ Pa. A emitting layer of bis[(8-hydroxyquinolino)(salicylidene-o-hydroxyanilino)gallium]($Ga_2(saph)_2q_2$) doped with 4-(dicyanomethylene)-2-t-butyl-6-(1,1,7,7-tetramethyljulolidyl-9-enyl)-4H-pyran(DCJTB)(600 angstroms) was then deposited onto the hole-transport layer by co-evaporation from two sources. The doping concentration can be from 0.5% to 10%. The deposit rate was about 0.1–0.2nm/s.

d) The substrate was put in the vacuum of $1 \times 10^{-5}$–$1 \times 10^{-4}$ Pa. On top of the $Ga_2(saph)_2q_2$:DCJTB layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When DCJTB was doped in $Ga_2(saph)_2q_2$ at 2.5% concentration, the light output from this EL device was 103 cd/m² when it was driven by a current source at 20 mA/cm². The maximum brightness of the device was up to 2980 cd/m² (at 24V) and the EL emission was at around 644 nm. The EL color is red with 1931 CIE color coordinates of X=0.673 and Y=0.325.

Example 86

An exemplary EL device satisfying the requirements of the invention was constructed in the following manner. The organic EL medium has three organic layers, namely, a hole transport layer, a doped emitting layer, an electron-transport layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) The substrate was put in the vacuum of $1 \times 10^{-5}$–$1 \times 10^{-4}$ Pa. A hole transport layer of N,N'-bis-(1-naphthyl)-N,N'-diphenylbenzidine (400 Angstroms) was then deposited on top of the ITO coated substrate by evaporation. The deposit rate was about 0.1–0.2 nm/s.

c) The substrate was put in the vacuum of $1 \times 10^{-5}$–$1 \times 10^{-4}$ Pa. A emitting layer of bis[(8-hydroxyquinolino)(salicylidene-o-hydroxyanilino)gallium]($Ga_2(saph)_2q_2$) doped with 4-(dicyanomethylene)-2-t-butyl-6-(1,1,7,7,-tetramethyljulolidyl-9-enyl)-4H-pyran (DCJTB)(600 Angstroms) was then deposited onto the hole-transport layer by co-evaporation from two sources. The doping concentration can be from 0.5% to 10%. The deposit rate was about 0.1–0.2 nm/s.

d) The substrate was put in the vacuum of $1 \times 10^{-5}$–$1 \times 10^{-4}$ Pa. A electron-transport layer of $Alq_3$ (200 Angstroms) was then deposited onto the luminescent layer by evaporation. The deposit rate was about 0.1–0.2 nm/s.

e) The substrate was put in the vacuum of $1 \times 10^{-5}$–$1 \times 10^{-4}$ Pa. On top of the $Alq_3$ layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When DCJTB was doped in $Ga_2(saph)_2q_2$ at 2.0% concentration, the light output from this EL device was 298 cd/m² when it was driven by a current source at 20 mA/cm². The EL emission was at around 652 nm. The EL color is red with 1931 CIE color coordinates of X=0.655 and Y=0.343.

Example 87

An exemplary EL device satisfying the requirements of the invention was constructed in the following manner. The organic EL medium has three organic layers, namely, a hole transport layer, a doped emitting layer, an electron-transport layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) The substrate was put in the vacuum of $1 \times 10^{-5}$–$1 \times 10^{-4}$ Pa. A hole transport layer of N,N'-bis-(1-naphthyl)-N,N'-diphenylbenzidine (400 Angstroms) was then deposited on top of the ITO coated substrate by evaporation. The deposit rate was about 0.1–0.2 nm/s.

c) The substrate was put in the vacuum of $1 \times 10^{-5}$–$1 \times 10^{-4}$ Pa. A emitting layer of bis[(8-hydroxyquinolino)(salicylidene-o-hydroxyanilino)gallium](Ga$^2$(saph)$_2$q$_2$) doped with 4-(dicyanomethylene)-2-t-butyl-6-(1,1,7,7-tetramethyljulolidyl-9-enyl)-4H-pyran (DCJTB)(600 Angstroms) was then deposited onto the hole-transport layer by co-evaporation from two sources. The doping concentration can be from 0.5% to 10%. The deposit rate was about 0.1–0.2 nm/s.

d) The substrate was put in the vacuum of $1\times10^{-5}$–$1\times10^{-4}$ Pa. A electron-transport layer of Ga$_2$(saph)$_2$q$_2$ (200 Angstroms) was then deposited onto the luminescent layer by evaporation.

e) The substrate was put in the vacuum of $1\times10^{-5}$–$1\times10^{-4}$ Pa. On top of the Ga$_2$(saph)$_2$q$_2$ layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When DCJTB was doped in Ga$_2$(saph)$_2$q$_2$ at 1.0% concentration, the light output from this EL device was 438 cd/m$^2$ when it was driven by a current source at 20 mA/cm$^2$. The maximum brightness of the device was up to 7027 cd/m$^2$ (at 11.7V) and the EL emission was at around 628 nm. The EL color is red with 1931 CIE color coordinates of x=0.633 and y=0.364

When DCJTB was doped in Ga$_2$(saph)$_2$q$_2$ at 2.0% concentration, the light output from this EL device was 421 cd/m$^2$ when it was driven by a current source at 20 mA/cm$^2$. The maximum brightness of the device was up to 7260 (at 20V) and the EL emission was at around 640 nm. The EL color is red with 1931 CIE color coordinates of x=0.675 and y=0.322.

EL Device Fabrication by Solution Process and their Performance

An EL device satisfying the requirements of the invention was constructed in the following manner. The organic EL medium has anode, organic layers and cathode. And these organic layers was spin-coated or screen-printed from the corresponding solution

Example 88

An exemplary EL device satisfying the requirements of the invention was constructed in the following manner. The organic EL medium has two organic layers, namely, a hole injection and transport layer, an emitting and electron-transport layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) An emitting layer of bis[(2,2,6,6-tetramethyl-3,5-heptanedione)(salicylidene-o-hydroxyanilino) aluminum] ([Al (saph)DPM]$_2$, Complex IV-1, 500–1000 Angstroms) was then deposited on top of a PEDOT/PSS layer by spin-coating from tetrahydrofuran(THF) solution(with a concentration from 1 mg–10 mg/ml.

d) On top of the above two layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

The light output from this EL device was 45 cd/m$^2$ when it was driven by a current source at 20 mA/cm$^2$. The device has a turn-on voltage of approximately 7V and provides a luminance of 220 cd/m$^2$ at 14V. The EL emission was green at around 540 nm.

Example 89

An exemplary EL device satisfying the requirements of the invention was constructed in the following manner. The organic EL medium has two organic layers; namely, a hole injection and transport layer, and a doped emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) An emitting layer of bis[(2,2,6,6-tetramethyl-3,5-heptanedione)(salicylidene-o-hydroxyanilino)aluminum] ([Al (saph)DPM]$_2$, Complex IV-1, 500–1000 Angstroms) doped rubrene was then deposited on top of a PEDOT/PSS layer by spin-coating from tetrahydrofuran (THF) solution. The doping concentration can be from 0.5 wt %–10 wt %.

d) On top of the above two layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When the doping concentration of 1 wt %, the light output from this EL device was 60 cd/m$^2$ when it was driven by a current source at 20 mA/cm$^2$. The device has a low turn-on voltage of 5V and a maximum luminance of 515 cd/m$^2$ at 17V. The EL emission was yellow at around 550–560 nm.

Example 90

An exemplary EL device satisfying the requirements of the invention was constructed in the following manner. The organic EL medium has three organic layers; namely, a hole injection layer, a hole transport layer, and an emitting and electron-transport layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) On top of PEDOT/PSS layer, a hole transport layer of methoxy-substituted 1,3,5-tris[4-(diphenylamino)phenyl] benzene (TDAPB) can be deposited from tetrahydrofuran solution. The concentration can be from 0.5 wt % to 5 wt %.

d) An emitting layer of bis[(2,2,6,6-tetramethyl-3,5-heptanedione)(salicylidene-o-hydroxyanilino)aluminum] ([Al(saph)DPM]$_2$, Complex IV-1, 500–1000 Angstroms) was then spin-coated on top of the (PEDOT/PSS)/TDAPB layer stack from methanol solution (with a concentration of 5 mg/ml).

e) On top of the above organic layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

The light output from this EL device was 60 cd/m$^2$ when it was driven by a current source at 20 mA/cm$^2$. The device has a turn-on voltage of approximately 5V and provides a luminance of 760 cd/m$^2$ at 14V. The EL emission was green at around 540 nm.

Example 91

An exemplary EL device satisfying the requirements of the invention was constructed in the following manner. The organic EL medium has three organic layers; namely, a hole injection layer, a hole transport layer, and a doped emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) On top of PEDOT/PSS layer, a hole transport layer of methoxy-substituted 1,3,5-tris[4-(diphenylamino)phenyl]benzene (TDAPB) can be deposited from tetrahydrofuran solution. The concentration can be from 0.5% to 5%.

d) An emitting layer of bis[(2,2,6,6-tetramethyl-3,5-heptanedione)(salicylidene-o-hydroxyanilino) aluminum] ([Al(saph)DPM]$_2$, Complex IV-1, 500–1000 Angstroms) doped rubrene was spin-coated on top of a PEDOT/PSS layer from methanol solution. The doping concentration can be from 0.5–10 wt %.

e) On top of the above two layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When the doping concentration of 1 wt %, the light output from this EL device was 60 cd/m$^2$ when it was driven by a current source at 20 mA/cm$^2$. The device has a low turn-on voltage of 5V and a maximum luminance of 515 cd/m$^2$ at 17V. The EL emission was yellow at around 550–560 nm.

Example 92

An exemplary EL device satisfying the requirements of the invention was constructed in the following manner. The organic EL medium has three organic layers, namely, a hole injection, a hole transport layer, an doped emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) On top of PEDOT/PSS layer, a hole transport layer of methoxy-substituted 1,3,5-tris[4-(diphenylamino)phenyl]benzene (TDAPB) can be deposited from tetrahydrofuran solution. The concentration can be from 0.5 wt % to 5 wt %.

d) An emitting layer of bis[(2,2,6,6-tetramethyl-3,5-heptanedione)(salicylidene-o-hydroxyanilino)aluminum] doped with DCJTB was then spin-coated on top of the (PEDOT/PSS)/TDAPB layer stack from methanol solution. The doping concentration could be from 0.5–10 wt % e) On top of the above organic layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When DCJTB was doped in [Al(saph)DPM]$_2$ at 2.0% concentration, the light output from this EL device was 78 cd/m$^2$ when it was driven by a current source at 20 mA/cm$^2$. The device has a turn-on voltage of approximately 5V and provides a luminance of 759 cd/m$^2$ at 14V. The EL emission was red at around 628 nm.

Example 93

An exemplary EL device satisfying the requirements of the invention was constructed in the following manner. The organic EL medium has three organic layers, namely, a hole injection, a hole transport layer, an doped emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) On top of PEDOT/PSS layer, a hole transport layer of methoxy-substituted 1,3,5-tris[4-(diphenylamino)phenyl]benzene (TDAPB) can be deposited from tetrahydrofuran solution. The concentration can be from 0.5% to 5%.

d) An emitting layer of bis[(2,2,6,6-tetramethyl-3,5-heptanedione)(salicylidene-o-hydroxyanilino) aluminum] doped with quinacridone (QA) was then spin-coated on top of the (PEDOT/PSS)/TDAPB layer stack from methanol solution. The doping concentration could be from 0.5–10 wt % e) On top of the above organic layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When QA was doped in [Al(saph)DPM]$_2$ at 2.0 wt % concentration, the light output from this EL device was 79 cd/m$^2$ when it was driven by a current source at 20 mA/cm$^2$.

The device has a turn-on voltage of approximately 5V and provides a luminance of 864 cd/m² at 14V. The EL emission was red at around 540 nm.

Example 94

An exemplary EL device satisfying the requirements of the invention was constructed in the following manner. The organic EL medium has three organic layers; namely, a hole injection, a hole transport layer, and a doped emitting layer.

a) An indium-tin-oxide (ITO) coated glass substrate was sequentially ultrasonically cleaned in a commercial detergent, rinsed in deionized water, degreased in toluene vapor and exposed to ultraviolet light and ozone for a few minutes.

b) A hole injection layer of PEDOT/PSS (poly(3,4-ethylenedioxythiophene)/poly(styrenesulfonate), 1:1, 500–1000 Angstroms) was then deposited on top of the ITO coated substrate by spin coating from aqueous solution. (Further information on this polymer system, which is available from Bayer AG, is given in Bayer's Provisional Product Information Sheet for Trial Product Al 4071).

c) On top of PEDOT/PSS layer, a hole transport layer of methoxy-substituted 1,3,5-tris[4-(diphenylamino)phenyl] benzene (TDAPB) can be deposited from tetrahydrofuran solution. The concentration can be from 0.5% to 5%.

d) An emitting layer of bis[(2,2,6,6-tetramethyl-3,5-heptanedione)(salicylidene-o-hydroxyanilino) aluminum] doped with rubrene was then spin-coated on top of the (PEDOT/PSS)/TDAPB layer stack from methanol solution. The doping concentration could be from 0.5–10 wt 10% e) On top of the above organic layers was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

When rubrene was doped in [Al(saph)DPM]₂ at 2.0 wt % concentration, the light output from this EL device was 123 cd/m² when it was driven by a current source at 20 mA/cm². The device has a turn-on voltage of approximately 5V and provides a luminance of 1025 cd/m² at 14V. The EL emission was red at around 550–560nm.

Example 95

According to example 84, an exemplary EL device can be fabricated by replacing the ITO-coated substrate with plastic substrate of ITO-coated poly (ethylene-terephthalate)(PET).

The light output from this EL device was 40 cd/m² when it was driven by a current source at 20 mA/cm². The device has a turn-on voltage of approximately 7V and provides a luminance of 250 cd/m² at 14V. The EL emission was green at around 540 nm.

Example 96

According to example 85, an exemplary EL device can be fabricated by replacing the ITO-coated substrate with plastic substrate of ITO-coated poly (ethylene-terephthalate)(PET).

When the doping concentration of 1 wt %, the light output from this EL device was 78 cd/m² when it was driven by a current source at 20 mA/cm². The device has a low turn-on voltage of 5V and a maximum luminance of 565 cd/m² at 17V. The EL emission was yellow at around 550–560 nm.

Example 97

According to example 92 an exemplary EL device can be fabricated by replacing the ITO-coated substrate with plastic substrate of ITO-coated poly (ethylene-terephthalate)(PET).

When DCJTB was doped in [Al(saph)DPM]₂ at 2.0% concentration, the light output from this EL device was 78 cd/m² when it was driven by a current source at 35 mA/cm². The device has a turn-on voltage of approximately 5V and provides a luminance of 659 cd/m² at 14V. The EL emission was red at around 628 nm.

Example 98

According to example 93, an exemplary EL device can be fabricated by replacing the ITO-coated substrate with plastic substrate of ITO-coated poly (ethylene-terephthalate)(PET).

When QA was doped in [Al(saph)DPM]₂ at 2.0 wt % concentration, the light output from this EL device was 75 cd/m² when it was driven by a current source at 20 mA/cm². The device has a turn-on voltage of approximately 5V and provides a luminance of 764 cd/m² at 14V. The EL emission was red at around 540 nm.

Example 99

According to example 94, an exemplary EL device can be fabricated by replacing the ITO-coated substrate with plastic substrate of ITO-coated poly (ethylene-terephthalate)(PET).

When rubrene was doped in [Al(saph)DPM]₂ at 2.0 wt % concentration, the light output from this EL device was 123 cd/m² when it was driven by a current source at 46 mA/cm². The device has a turn-on voltage of approximately 5V and provides a luminance of 925 cd/m² at 14V. The EL emission was red at around 550–560 nm.

The invention has been described in detail with particular reference to certain preferred embodiments thereof, but it will be understood that variations and modifications can be effected within the spirit and scope of the invention.

What is claimed:

1. A compound of the formula:

wherein;

M is a trivalent metal selected from the group consisting of Al, Ga, In and Tl;

n is 2;

$L^2$ is a bidentate ligand, comprising one oxygen atom and one nitrogen atom to coordinate the central ion, selected from the group consisting of unsubstituted 8-hydroxyquinoline;
unsubstituted 2-(o-hydroxyphenyl)-benzoxazole;
unsubstituted 4-hydroxy-1,5-naphthyridine;
unsubstituted 5-hydroxyquinoxaline;
unsubstituted 2-(o-hydroxylphenyl)-benzimidazole;
unsubstituted 2-(o-hydroxylphenyl)-benzothiazole;
unsubstituted 10-hydroxyl-benzoquinoline;
unsubstituted 2-carboxyl-pyridine;
substituted 8-hydroxyquinoline;
substituted 2-(o-hydroxyphenyl)-benzoxazole;
substituted 4-hydroxy-1,5-naphthyridine;
substituted 5-hydroxyquinoxaline;
substituted 2-(o-hydroxylphenyl)-benzimidazole;
substituted 2-(o-hydroxylphenyl)-benzothiazole;
substituted 10-hydroxyl-benzoquinoline;
substituted 2-carboxyl-pyridine; and substituent groups include alkyl groups having 1–8 carbon atoms, groups having at least one halogen atom, cyano groups, amino groups, amido groups, sulfonyl groups, carbonyl groups, aryl groups, and heteroalkyl groups; and L³ is a tridentate ligand with three chelate points and has the formula

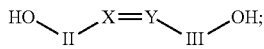

in which

X and Y independently represent one of CH and N; and

II and III are selected from the group consisting of unsubstituted aryl groups, unsubstituted heteroalkyl groups, substituted aryl groups, and substituted heteroalkyl groups.

2. The compound according to claim 1, wherein: X=CH and Y=N whereby L³ has the formula:

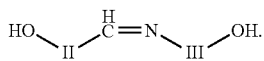

3. The compound according to claim 1, wherein: X=CH and Y=CH whereby L³ has the formula:

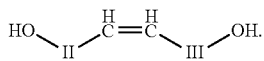

4. The compound according to claim 1, wherein: X=Y=N whereby L³ has the formula:

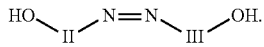

5. A compound of the formula:

wherein;

M is a trivalent metal selected from the group consisting of Al, Ga, In and Tl;

n is 2;

L² is a bidentate ligand, comprising two oxygen atoms to coordinate the central ion, selected from the group consisting of unsubstituted β-diketone, substituted β-diketone, unsubstituted enol, and substituted enol; and L³ is a tridentate ligand with three chelate points and has the formula;

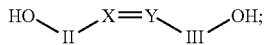

in which

X and Y independently represent one of CH and N;

II, III are selected from the group consisting of unsubstituted aryl groups, unsubstituted heteroalkyl groups, substituted aryl groups, and substituted heteroalkyl groups; and substituent groups include alkyl groups having 1–8 carbon atoms, groups having at least one halogen atom, cyano groups, amino groups, amido groups, sulfonyl groups, carbonyl groups, aryl groups, and heteroalkyl groups.

6. The compound according to claim 5, wherein: X=CH and Y=N whereby L³ has the formula:

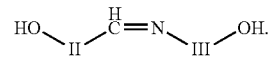

7. The compound according to claim 5, wherein: X=CH and Y=CH whereby L³ has the formula:

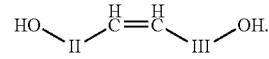

8. The compound according to claim 5, wherein: X=Y=N whereby L³ has the formula:

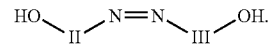

9. A compound according to claim 1, wherein:
L² is one of unsubstituted 8-hydroxyquinoline and substituted 8-hydroxyquinoline;
L³ is a tridentate of schiff-base ligand; and
the trivalent metal M is Ga.

10. A compound according to claim 1, wherein:
L² is one of unsubstituted 8-hydroxyquinoline and substituted 8-hydroxyquinoline;
L³ is a tridentate of stilbene ligand; and
the trivalent metal M is Ga.

11. The compound according to claim 1, wherein:
L² is one of unsubstituted 8-hydroxyquinoline and substituted 8-hydroxyquinoline;
L³ is a tridentate of azobenzene ligand; and
the trivalent metal M is Ga.

12. The compound according to claim 5, wherein:
L² is one of unsubstituted acetylacetone and substituted acetylacetone;
L³ is a tridentate of schiff-base ligand;
the trivalent metal M is Al; and
n equals 2.

13. The compound according to claim 5, wherein:
L² is one of unsubstituted acetylacetone and substituted acetylacetone;
L³ is a tridentate of stilbene ligand;
the trivalent metal M is Al; and
n equals 2.

14. The compound according to claim 5, wherein:
L² is one of unsubstituted acetylacetone and substituted acetylacetone;
L³ is a tridentate of azobenzene ligand;
the trivalent metal M is Al; and
n equals 2.

15. An organic light emitting device comprising:
an anode;
a cathode; and
at least one organic luminescent layer formed of a luminescent material including a compound of the formula:

wherein;

M is a trivalent metal selected from the group consisting of Al, Ga, In and Tl;

n is 2;

$L^2$ is a bidentate ligand, comprising one oxygen atom and one nitrogen atom to coordinate the central ion, selected from the group consisting of unsubstituted 8-hydroxyquinoline;
unsubstituted 2-(o-hydroxyphenyl)-benzoxazole;
unsubstituted 4-hydroxy-1,5-naphthyridine;
unsubstituted 5-hydroxyquinoxaline;
unsubstituted 2-(o-hydroxylphenyl)-benzimidazole;
unsubstituted 2-(o-hydroxylphenyl)-benzothiazole;
unsubstituted 10-hydroxyl-benzoquinoline;
unsubstituted 2-carboxyl-pyridine;
substituted 8-hydroxyquinoline;
substituted 2-(o-hydroxyphenyl)-benzoxazole;
substituted 4-hydroxy-1,5-naphthyridine;
substituted 5-hydroxyquinoxaline;
substituted 2-(o-hydroxylphenyl)-benzimidazole;
substituted 2-(o-hydroxylphenyl)-benzothiazole;
substituted 10-hydroxyl-benzoquinoline; and
substituted 2-carboxyl-pyridine; and substituent groups include alkyl groups having 1–8 carbon atoms, halogen, cyano groups, amino groups, amido groups, sulfonyl groups, carbonyl groups, aryl groups, and heteroalkyl groups; and $L^3$ is a tridentate ligand with three chelate points and has the formula;

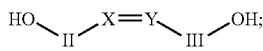

in which

X and Y independently represent one of CH and N; and

II and III are selected from the group consisting of unsubstituted aryl groups, unsubstituted heteroalkyl groups, substituted aryl groups, and substituted heteroalkyl groups.

16. An organic light emitting device comprising:

an anode;

a cathode; and at least one organic luminescent layer formed of a luminescent material including a compound of the formula:

$(L^2L^3M)_n$;

wherein;

M is a trivalent metal selected from the group consisting of Al, Ga, In and Tl;

n is 2;

$L^2$ is a bidentate ligand, comprising two oxygen atoms to coordinate the central ion, selected from the group consisting of unsubstituted β-diketone, substituted β-diketone, unsubstituted enol, and substituted enol; and $L^3$ is a tridentate ligand with three chelate points and has the formula

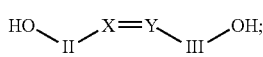

in which

X and Y independently represent one of CH and N;

II, III are selected from the group consisting of unsubstituted aryl groups, unsubstituted heteroalkyl groups, substituted aryl groups, and substituted heteroalkyl groups; and substituent groups include alkyl groups having 1–8 carbon atoms, halogen, cyano groups, amino groups, amido groups, sulfonyl groups, carbonyl groups, aryl groups, and heteroalkyl groups.

17. An organic light emitting device according to claim 15, wherein:

$L^2$ is one of unsubstituted 8-hydroxyquinoline and substituted 8-hydroxyquinoline;

$L^3$ is a tridentate of schiff-base ligand; and the trivalent metal M is Ga.

18. An organic light emitting device according to claim 15, wherein:

$L^2$ is one of unsubstituted 8-hydroxyquinoline and substituted 8-hydroxyquinoline;

$L^3$ is a tridentate of stilbene ligand; and the trivalent metal M is Ga.

19. An organic light emitting device according to claim 15, wherein:

$L^2$ is one of unsubstituted 8-hydroxyquinoline and substituted 8-hydroxyquinoline;

$L^3$ is a tridentate of azobenzene ligand; and the trivalent metal M is Ga.

20. An organic light emitting device according to claim 16, wherein:

$L^2$ is one of unsubstituted acetylacetone and substituted acetylacetone;

$L^3$ is a tridentate of schiff-base ligand;

the trivalent metal M is Al; and n equals 2.

21. An organic light emitting device according to claim 18; wherein the organic layers are formed by at least one of spin coating and ink-jet printing.

22. An organic light emitting device according to claim 16, wherein:

$L^2$ is one of unsubstituted acetylacetone and substituted acetylacetone;

$L^3$ is a tridentate of stilbene ligand;

the trivalent metal M is Al; and n equals 2.

23. An organic light emitting device according to claim 22, wherein the organic layers are formed by at least one of spin coating and ink-jet printing.

24. An organic light emitting device according to claim 16, wherein:

$L^2$ is one of unsubstituted acetylacetone and substituted acetylacetone;

$L^3$ is a tridentate of azobenzene ligand;

the trivalent metal M is Al; and n equals 2.

25. An organic light emitting device according to claim 24, wherein the organic layers are formed by at least one of spin coating and ink-jet printing.

* * * * *